US009708871B2

(12) United States Patent
Larson

(10) Patent No.: US 9,708,871 B2
(45) Date of Patent: Jul. 18, 2017

(54) APPARATUS AND METHOD FOR CONTROLLING, MEASURING, AND SAMPLING A FLUID FLOW

(71) Applicant: National Oilwell Varco, L.P., Houston, TX (US)

(72) Inventor: Thomas Robert Larson, Montgomery, TX (US)

(73) Assignee: National Oilwell Varco, L.P., Houston, TX (US)

( * ) Notice: Subject to any disclaimer, the term of this patent is extended or adjusted under 35 U.S.C. 154(b) by 452 days.

(21) Appl. No.: 14/190,568

(22) Filed: Feb. 26, 2014

(65) Prior Publication Data
US 2014/0251689 A1    Sep. 11, 2014

Related U.S. Application Data

(60) Provisional application No. 61/774,367, filed on Mar. 7, 2013.

(51) Int. Cl.
*E21B 21/08*    (2006.01)
*G01F 1/00*    (2006.01)
(Continued)

(52) U.S. Cl.
CPC .............. *E21B 21/08* (2013.01); *G01F 1/002* (2013.01); *G01F 3/065* (2013.01); *G01N 1/2035* (2013.01);
(Continued)

(58) Field of Classification Search
CPC .......... E21B 21/08; G01F 1/002; G01F 3/065; G01F 23/296; G01N 1/2035; G01N 2001/2057
(Continued)

(56) References Cited

U.S. PATENT DOCUMENTS 665,620 A * 1/1901 Stephens et al. .... G01N 1/2035
73/863.02
1,170,842 A 2/1916 Newhouse
(Continued)

FOREIGN PATENT DOCUMENTS

DE    102009053316 A1    5/2011
EP    0042245 A1    12/1981
(Continued)

OTHER PUBLICATIONS

PCT International Search Report and Written Opinion dated Oct. 6, 2014, for International Application No. PCT/US2014/018974, 18 pages.
(Continued)

*Primary Examiner* — Lisa Caputo
*Assistant Examiner* — Nathaniel T Woodward
(74) *Attorney, Agent, or Firm* — Amerson Law Firm, PLLC

(57) ABSTRACT

An apparatus includes a body having a central axis, a fluid inlet coupled to the body, the fluid inlet being adapted to receive a flow of a fluid, and a fluid outlet coupled to the body. The fluid inlet and the fluid outlet are substantially coaxially aligned so as to define a flow axis through the apparatus, and the flow axis is laterally offset from and perpendicular to the central axis of the body. A rotating blade assembly is disposed within said body and includes a plurality of blades, wherein the rotating blade assembly is adapted to be controllably rotated about the central axis so as to control a fluid level of the flow of fluid entering the fluid inlet.

37 Claims, 12 Drawing Sheets

(51) Int. Cl.
*G01N 1/20* (2006.01)
*G01F 3/06* (2006.01)
*G01F 23/296* (2006.01)

(52) U.S. Cl.
CPC .... *G01F 23/296* (2013.01); *G01N 2001/2057* (2013.01)

(58) Field of Classification Search
USPC .............................................. 73/863.41, 863
See application file for complete search history.

(56) References Cited

U.S. PATENT DOCUMENTS

| | | | | |
|---|---|---|---|---|
| 1,985,173 A | * | 12/1934 | Kent | G01N 1/2035 73/863.02 |
| 3,690,179 A | | 9/1972 | Olson | |
| 4,145,914 A | * | 3/1979 | Newman | G01F 23/2962 331/1 A |
| 4,170,900 A | | 10/1979 | Ozawa | |
| 5,409,034 A | * | 4/1995 | Ostertag | E03C 1/05 137/499 |
| 2002/0134171 A1 | | 9/2002 | Champness | |
| 2004/0144427 A1 | * | 7/2004 | George | F24F 11/047 137/499 |

FOREIGN PATENT DOCUMENTS

| | | |
|---|---|---|
| EP | 0437872 A2 | 7/1991 |
| GB | 0042245 A1 * | 12/1981 ......... A01D 41/1271 |

OTHER PUBLICATIONS

PCT Partial International Search, Annex to Invitation to Pay Additional Fees dated Jun. 18, 2014, for International Application No. PCT/US2014/018974, 6 pages.

\* cited by examiner

APPARATUS AND METHOD FOR CONTROLLING, MEASURING, AND SAMPLING A FLUID FLOW

BACKGROUND

1. Field of the Disclosure

The subject matter disclosed herein is generally directed to methods and apparatuses for monitoring and measuring fluid that is flowing through a conduit. More specifically, the present disclosure is directed to systems, methods, and apparatuses that may be used for obtaining samples of a fluid flowing through a conduit, and/or for determining the flow rate of the fluid flowing through the conduit.

2. Description of the Related Art

Drilling fluids are used when drilling or completing wells for a variety of reasons. Common uses for drilling fluids include: lubrication and cooling of drill bit cutting surfaces, cleaning the wellbore and transportation of cuttings to the surface, controlling formation pressure, maintaining well stability, and transmitting hydraulic horsepower to downhole motors.

Drilling fluids are pumped down through the drill string to the drill bit. The drilling fluids pass through the drill bit and then are returned back to the surface through the annulus between the outside of the drill pipe and the wellbore wall. To control formation pressure, maintain wellbore stability, lubricate the drill bit, and provide other functions, drilling fluids often include suspended additives, including barites, clay, and other materials. These additives are blended with the drilling fluid at the surface so that the drilling fluid being pumped through the drill string into the wellbore has the desired properties.

As the drilling mud exits the drill bit and returns to the surface, it may become mixed with drill cuttings and fluids from the formation. In order to maintain the composition of the drilling fluid being pumped into the drill string, the drilling fluid is cleaned and treated at the surface before being recirculated into the well. During the cleaning and treating process, the drilling fluid can be tested at a variety of locations and time intervals to determine fluid characteristics such as density and viscosity. In many applications, the testing of drilling fluid commonly requires the direct involvement of rig personnel, who oftentimes must manually obtain samples of the drilling fluid. These manually obtained drilling fluid samples are then analyzed using a variety of testing equipment and procedures known in the art.

Depending on the specific drilling rig setup and the overall configuration of the drilling fluid circulation system, manually obtaining drill fluid samples in an effective manner may be problematic. Moreover, as the overall automation of many common drilling rig operations continues to increase, it is recognized that automating the drilling fluid sample acquisition activity, that is, obtaining samples without the direct involvement of rig personnel, may also be advantageous.

One problem that must sometimes be addressed is the loss of circulation materials, i.e., drilling mud and its constituents, to the formation during the drilling operation. Depending on the characteristics of the geological formations being drilling through and the formulation of the drilling mud, a portion of the drilling mud may flow into one or more of the formations instead of returning up the annulus of the wellbore. In such cases, it can be difficult to adequately control pressures within wellbore since the hydrostatic load of the drilling fluid on the formation can be reduced below optimum levels. Furthermore, an increase of returned drilling fluid volume can sometimes occur, which may also be detrimental to the drill fluid characteristics. For example, the returned drilling fluid volume can increase due to the influx of liquids, gases, or both from the surrounding formation. In the event that the volume increase is due to additional liquid, then the mud weight can drop and the system used to control mud weight must make adjustments relatively quickly in order to maintain the proper pressure conditions within the well.

Accordingly, it is important to continuously monitor the flow rate of drilling fluid into the well versus the flow rate of the mixture of drilling fluid and drill cuttings, i.e., the drilling fluid mixture, back out of the well during the drilling operation so that the proper drilling environment, i.e., pressure and stability, is maintained within the wellbore. For example, when the flow rate of returned drilling fluid drops below the flow rate of drilling fluid into the well, the amount of drilling fluid pumped into the well can be increased in order to maintain the proper pressure gradient in the well. Additionally, in such cases the formulation of the drilling fluid can be adjusted to include so-called "lost circulation materials," can reduce or even prevent the loss of drilling fluid into the surrounding formation by blocking and/or plugging porous areas in the walls of the wellbore. Accordingly, the ability to accurately monitor the flow rate of the returning drilling fluid in real time can often be an important aspect of an overall drilling operation.

In some prior art drilling applications, a "paddle wheel" type flow indicator is sometimes used to obtain an estimation of the flow rate of returned drilling fluid mixture through a flowline. In a paddle wheel type flow indicator, the paddle wheel—which typically consists of plurality of radial blades, or paddles, mounted on a rotating wheel—"floats" on the upper surface of the drilling fluid as the fluid flows through the flow line. In some cases, paddle wheel is mounted on a hinged support arm, which allows the paddle wheel to move up or down along an arc defined by the hinged support arm so that paddle wheel stays substantially on contact with the upper surface of the drilling fluid as the drilling fluid level changes within the flow line.

However, the prior art paddle wheel flow indicator has several limitations that are due at least in part to the fact that the paddle wheel, by design, only contacts the upper surface of the flowing drilling fluid. For example, since the paddle wheel normally floats along the upper surface of the drilling fluid as it flows through the flow line, it can only measure a surface velocity of the flowing drilling fluid, and not a true volumetric flow of the fluid. Furthermore, as drilling progresses during a typical drilling operation and drilling fluid and drill cuttings are returned from the wellbore, a bed of stationary drill cuttings may tend to build up, at least temporarily, in the bottom of the flow line, e.g., below the paddle wheel. Therefore, the accuracy of the paddle wheel flow indicator can be compromised as there is no way to accurately ascertain how much of the cross sectional area of the flow line has gradually become at least partially occluded by a bed of stationary drill cuttings that is sporadically present below the paddle wheel. Moreover, assuming that a substantially constant volumetric flow of returned drilling fluid is flowing through the flow line, the surface velocity of the drilling fluid—as measured by the paddle wheel—will gradually increase as the bed of stationary drill cuttings build up due to the partially occluded, i.e., reduced, flow area through which the returned drilling fluid flows.

This type of variation in the flow area of a flow can be further exacerbated during a common drilling operation known as a "sweep". During the sweep operation, a relatively small amount of highly viscous fluid, or a relatively short term burst of a high volumetric fluid flow, is pumped down the well in order to "sweep" the well-bore clean of any drill cuttings that may have been too heavy to be carried up by the standard mud rheology. When this sweep of high viscosity or high flow rate fluid returns the surface, it is highly turbulent and carries a large amount of coarse particles. This fluid returning from the sweep operation also acts to rinse away the bed of stationary drill cuttings from the bottom of the flow line relatively quickly, thus causing a significant increase in the cross-section area that is available for flow. Accordingly, after the flow effects of the sweep operation have passed and normal operation resumes, there can often be a substantial decrease in the surface velocity of the flowing drilling fluid for any given value of volumetric flow, due at least in part to the temporary absence of the stationary bed of drill cuttings in the bottom of the flow line.

In view of the foregoing, there is a continuing need to accurately monitor and measure a flow of drilling fluid through a conduit during well drilling operations. The present disclosure is directed to various systems, methods, and apparatuses that may be used to address at least some of the issues and problems outlined above.

SUMMARY OF THE DISCLOSURE

The following presents a simplified summary of the present disclosure in order to provide a basic understanding of some aspects disclosed herein. This summary is not an exhaustive overview of the disclosure, nor is it intended to identify key or critical elements of the subject matter disclosed here. Its sole purpose is to present some concepts in a simplified form as a prelude to the more detailed description that is discussed later.

In one illustrative embodiment, an apparatus includes a body having a central axis and a fluid inlet coupled to the body, wherein the fluid inlet is adapted to receive a flow of a fluid. The apparatus also includes, among other things, a fluid outlet that is also coupled to the body, wherein the fluid inlet and the fluid outlet are substantially coaxially aligned so as to define a flow axis through the apparatus, and the flow axis is laterally offset from and perpendicular to the central axis of said body. Additionally, the illustrative apparatus further includes and a rotating blade assembly that is disposed within the body and includes a plurality of blades, wherein the rotating blade assembly is adapted to be controllably rotated about the central axis so as to control a fluid level of the flow of fluid entering the fluid inlet.

In another exemplary embodiment, an apparatus is disclosed that includes, among other things, a body having a central axis, a fluid inlet coupled to the body, the fluid inlet being adapted to receive a flow of a fluid, and a fluid outlet coupled to the body. Additionally, the fluid inlet and the fluid outlet are substantially coaxially aligned so as to define a flow axis through the apparatus, and the flow axis is laterally offset from and perpendicular to the central axis of the body. Furthermore, the disclosed apparatus also includes a sample outlet that is disposed on the body, and a rotating blade assembly disposed within the body, wherein the rotating blade assembly includes a plurality of blades and is adapted to receive a sample portion of the flow of fluid entering the fluid inlet and to discharge the received sample portion out of the apparatus through the sample outlet.

Also disclosed herein is an illustrative method of operating a flow apparatus that includes introducing a flow of a flow mixture to a fluid inlet of the flow apparatus, wherein the fluid inlet is coupled to a body of the flow apparatus and has a flow axis that is laterally offset from and substantially perpendicular to a central axis of the body. The method further includes, among other things, controlling a fluid level of the flow of the flow mixture introduced to the fluid inlet, wherein controlling the fluid level includes at least one of increasing the fluid level and decreasing the fluid level by controllably rotating a blade assembly that includes a plurality of blades and is disposed within the body about the central axis while flowing the flow of the flow mixture through the flow apparatus.

BRIEF DESCRIPTION OF THE DRAWINGS

The disclosure may be understood by reference to the following description taken in conjunction with the accompanying drawings, in which like reference numerals identify like elements, and in which.

Figure 1:
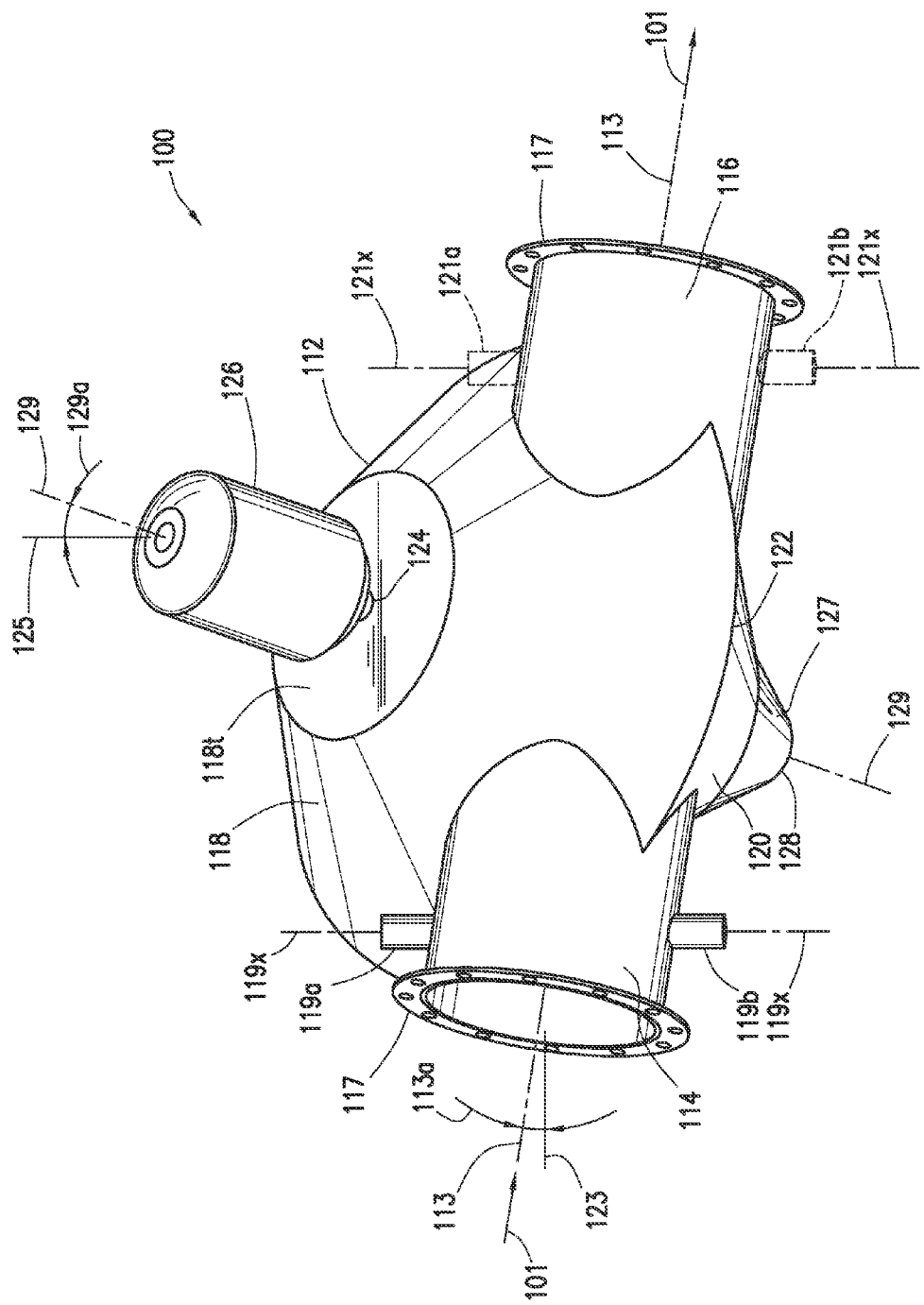
FIG. 1 is a perspective view of one illustrative embodiment of a fluid sampling and flow measurement apparatus of the present disclosure, wherein the central axis and the flow axis of the exemplary apparatus are arranged in one exemplary operating orientation.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

Various illustrative embodiments of the present subject matter are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various systems, structures and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

The subject matter disclosed herein is generally directed to systems, apparatuses, and methods for obtaining samples of a fluid flowing through a conduit without direct reliance upon manual intervention by sampling personnel—e.g., automatic sampling. Furthermore, the disclosed apparatuses may also be used as part of a flow measurement system that is adapted to determine the flow rate of fluid through a conduit that is coupled to the apparatus. For example, in certain illustrative embodiments, the apparatus may include a rotating blade assembly that is adapted to sweep, that is, remove, a sample portion of the fluid from the conduit for testing. Additionally, the disclosed apparatus may be operated in such a manner that the rotational velocity of the rotating blade assembly may be substantially proportional to the flow rate of fluid flowing through the conduit. Moreover, in at least some exemplary embodiments of the present disclosure, the apparatuses may be configured so that both the automatic sampling operation and the flow measurement operation are performed substantially simultaneously.

In the description set forth below, the various illustrative embodiments of the fluid sampling and flow measurement apparatus 100 shown in FIGS. 1-18 may hereinafter be referred to interchangeably as the "sampling apparatus 100," the "flow measurement apparatus 100," and/or the "apparatus 100." Accordingly, it should be understood that the terms "sampling apparatus 100," "flow measurement apparatus 100," and "apparatus 100" are each representative of the more broadly descriptive term "fluid sampling and flow measurement apparatus 100," and are therefore intended to describe and refer to the various embodiments disclosed herein.

FIGS. 1-7 depict one representative embodiment of a fluid sampling and flow measurement apparatus 100 in accordance with the present disclosure. FIG. 1 is a perspective view of the apparatus 100 when viewed from the flow line side thereof, and wherein the apparatus 100 has been arranged in an illustrative operating configuration, as will be further described below. FIGS. 2-7 are various elevation and plan views of the apparatus 100 wherein, for illustrative clarity, the central axis of the apparatus 100 has been oriented vertically and the flow axis of the apparatus 100 has been oriented horizontally.

In the exemplary embodiment illustrated in FIGS. 1-7, the fluid sampling and flow measurement apparatus 100 includes a body 112 having an upper portion 118 and a lower portion 120. In certain embodiments, the body 112 may be a substantially hollow thin shell fabricated from plates, such as steel plates and the like. In at least some embodiments, the upper shell portion 118 may have substantially a truncated conical shape, that is, a frustoconical shape, having a half cone angle 118a, as shown in FIGS. 1-7. Additionally, the upper shell 118 may have a substantially flat top plate 118t defining the upper boundary of the body 112. Depending on the specific design parameters of the body 112, the lower portion 120, e.g., the lower shell portion 120, may also have a substantially frustoconical shape with a half angle 120a.

Figure 5:
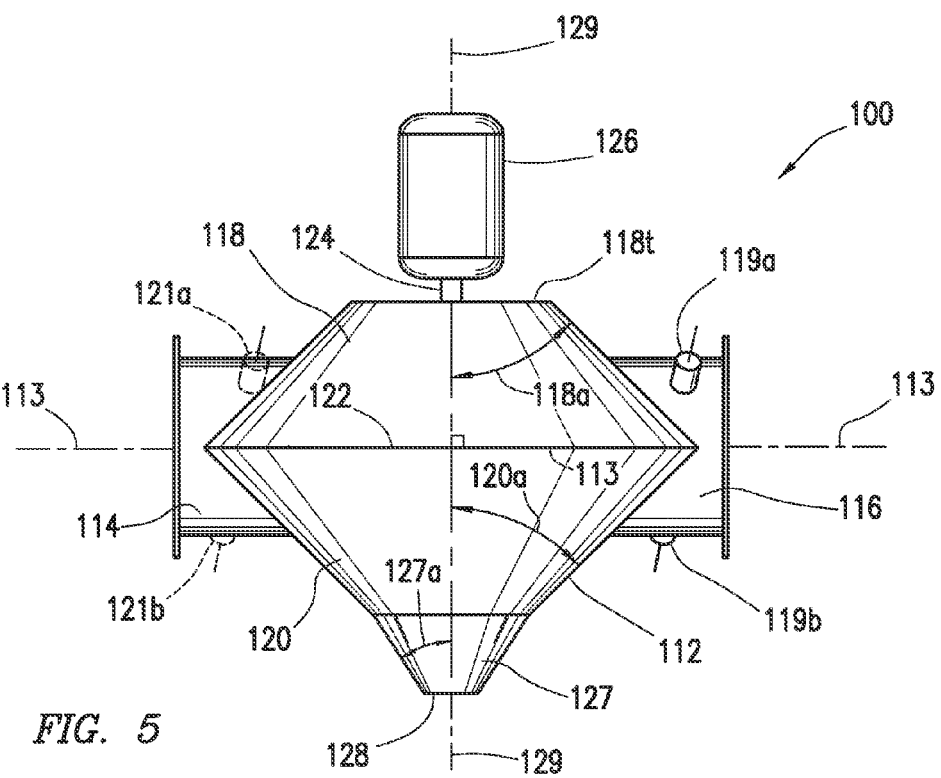
FIG. 5 is a back side elevation view of the illustrative fluid sampling and flow measurement apparatus of FIG. 1 taken along the view line "5-5" of FIG. 4.
Figure 6:
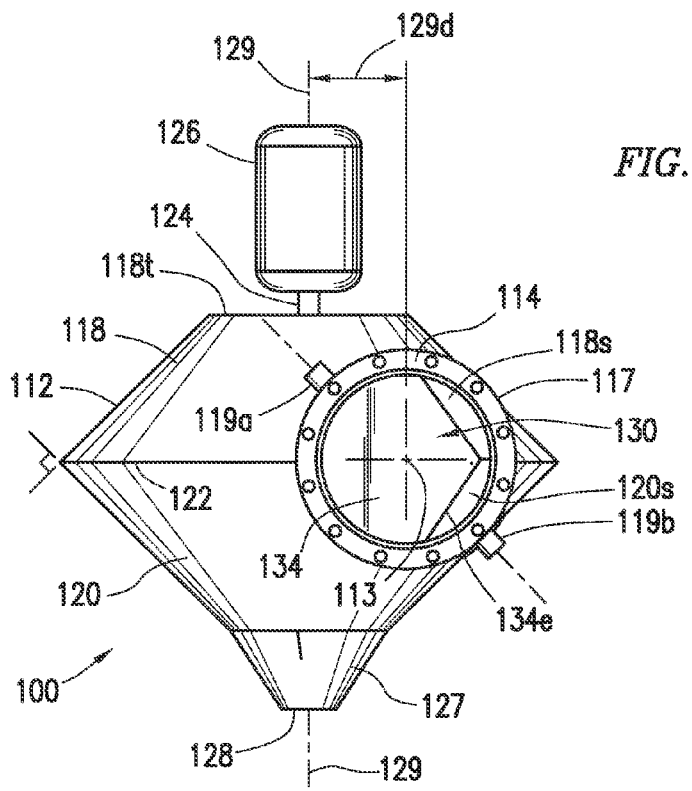
FIG. 6 is an inlet side elevation view of the exemplary fluid sampling and flow measurement apparatus of FIG. 1 taken along the view line "6-6" of FIG. 2.
Figure 7:
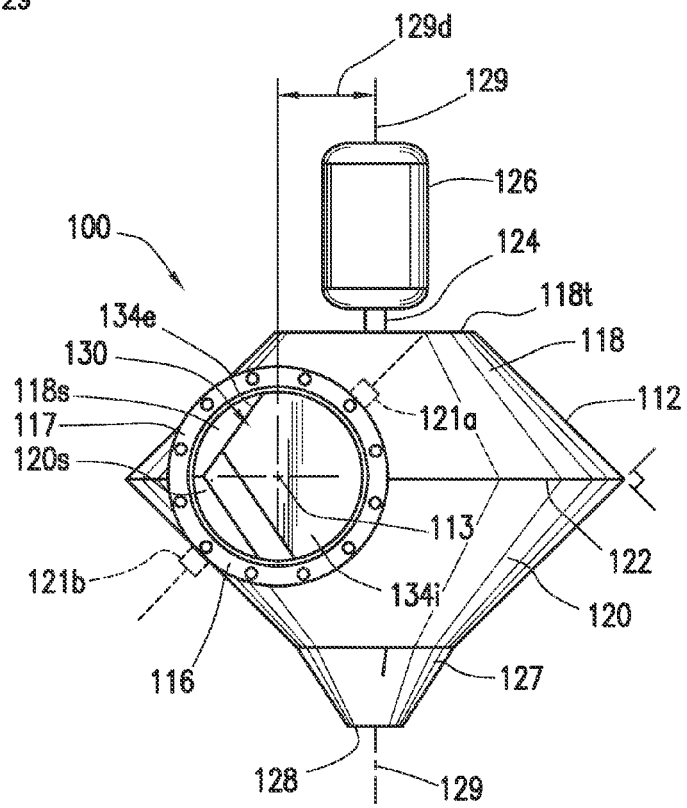
FIG. 7 is an outlet side elevation view of the illustrative fluid sampling and flow measurement apparatus of FIG. 1 taken along the view line "7-7" of FIG. 2.

In the illustrative embodiment depicted in FIGS. 1-7, the upper shell portion 118 and the lower shell portion 120 of the apparatus 100 intersect along a midline 122. Depending on the overall fabrication requirements for the apparatus, the upper shell portion 118 and the lower shell portion 120 may be independently constructed and then joined together so as to form the body 112, e.g., through welding, brazing, mechanical fasteners, and the like. In some embodiments, the half angles 118a and 120a may be substantially the same angle, although other angles and/or angle combinations may also be used. In at least one embodiment, the half angles 118a and 120a may each be approximately 45 degrees, in which case the upper shell portion 118 may be substantially perpendicular to the lower shell portion 120 where the two shell portions 118, 120 meet at the midline 122, as depicted in FIGS. 6 and 7.

Figure 18:
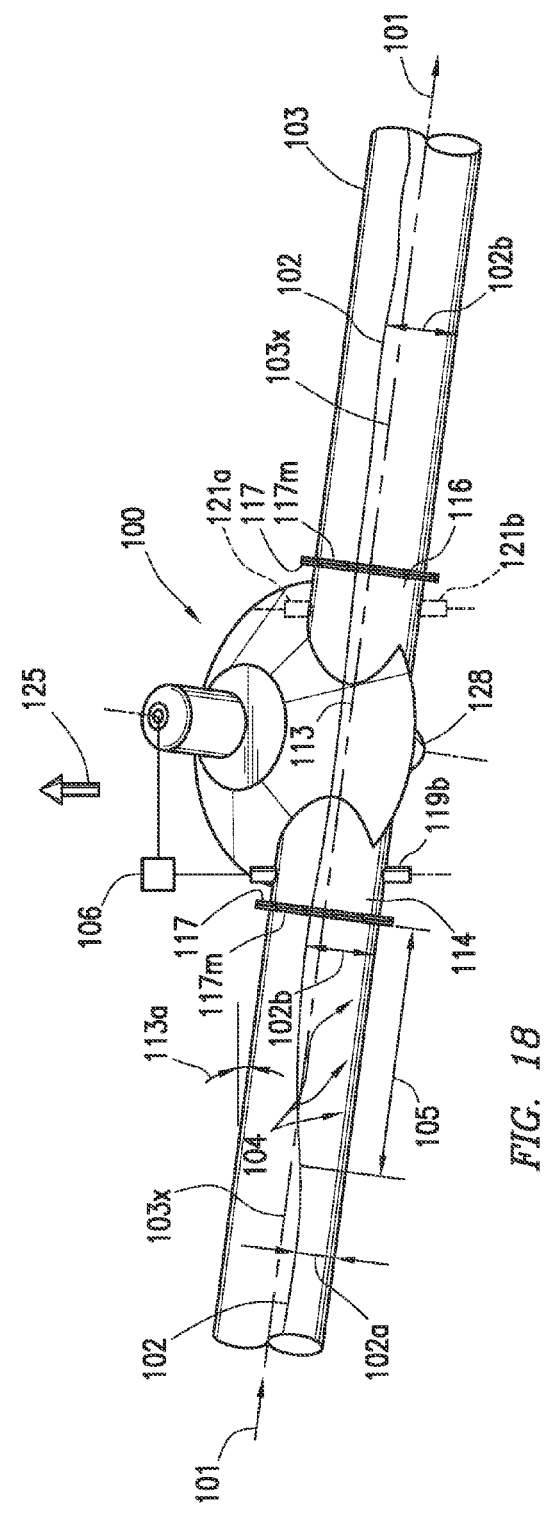
FIG. 18 is a side elevation view of one exemplary embodiment of a fluid sampling and flow measurement apparatus of the present disclosure when arranged in an illustrative flow line configuration.

As shown in FIGS. 1-7, the body 112 may also include a fluid inlet 114 and a fluid outlet 116, the centerline axes of which may be coaxial with and substantially define a flow axis 113 running through the body 112 of the apparatus 100. The fluid inlet 114 and fluid outlet 116 may also be adapted to be coupled to a conduit, e.g., a flow line, such as the flow line 103 shown in FIG. 18 (described below) via a suitably designed coupling 117 so that the flow axis 113 is substantially aligned with a flow axis 103x of the flow line 103 (FIG. 18). In certain embodiments, coupling 117 may be, for example, a flange, a hub connection, a weldment surface, a groove for a clamp, and the like, which thereby allows the fluid inlet 114 and the fluid outlet 116 to be coupled to a flow line. Fluid flowing through the fluid sampling and flow measurement apparatus 100 is generally along the flow axis 113 and in the direction of the flow arrows 101, that is, from the inlet 114 to the outlet 116.

One or both of the fluid inlet 114 and the fluid outlet 116 may be integrally formed with the body 112, the upper portion 118, or the lower portion 120. Furthermore, either one or both of the fluid inlet and outlet 114, 116 may be separately constructed and thereafter coupled to the body 112 via welding, brazing, mechanical fasteners, and the like, as previously described.

In at least some illustrative embodiments, one or more sensors 119 may be coupled to the fluid inlet 114. For example, as shown in FIGS. 1-7, an upper sensor 119a may be positioned on the top side of the fluid inlet 114, and in at least one embodiment, a lower sensor 119b may also be positioned on the bottom side of the fluid inlet 114. Depending on the desired operational parameters of the fluid sampling and flow measurement apparatus 100, the sensors 119a/b may be pressure sensors, capacitance sensors, level sensors, ultrasonic transceivers, and the like. Furthermore, the sensors 119a/b may be adapted to obtain data that indicates the presence and/or the amount of fluid flowing into the fluid inlet 114 from upstream of the apparatus 100. For example, in some embodiments, the sensors 119a/b may be adapted to obtain certain relevant data about the fluid as it flows into the apparatus 100, such as fluid level and the like. The sensor data obtained by the sensors 119a/b may then be used to quantitatively determine the flow rate of fluid flowing through the fluid inlet 114, which may in turn be used to control at least some operational parameters of the apparatus 100, as will be further described in conjunction with FIG. 18 below. In certain embodiments, the sensors 119a/b may include, for example, a pressure sensor, a capacitance sensor, a level sensor, an ultrasonic transceiver, and the like. For example, in one illustrative embodiment, the upper sensor 119a may be a level sensor and the lower sensor 119b may be a pressure sensor, although it should be understood that other types and combinations sensors may also be used. Additionally, as may be required for some applications, downstream sensors 121a/b may be similarly positioned on the fluid outlet 116, as indicated by dashed lines in FIGS. 1-7.

As shown in illustrative embodiments of FIGS. 1-7, the fluid sampling and flow measurement apparatus 100 may include a rotatable shaft 124 that extends through the top plate 118t of the upper shell portion 118 and is coupled to a drive motor 126. Depending on the overall design parameters of the apparatus 100, the motor 126 may be mounted directly to the body 112, or it may be separately supported independently of the body 112. For clarity, the various means for mounting and/or supporting the drive motor 126 are not shown. Furthermore, the motor 126 may also be operatively coupled to a suitable power source (not shown), such as an electrical, hydraulic, and/or pneumatic power source, and the like.

In certain embodiments, e.g., wherein the apparatus 100 is a fluid sampling apparatus 100 that is used to obtain a sample of a fluid flowing through a conduit, a sample outlet 128 may be disposed at the bottom end of the lower shell portion 120. In some exemplary configuration, the sample outlet 128 may be substantially coaxially aligned with the central axis 129 of the body 112. As illustrated in FIGS. 3, 4, 6, and 7, the central axis 129 may be substantially perpendicular to and offset by a distance 129d from the flow axis 113 through the body 112. Depending the overall sampling system requirements, the sample outlet 128 may simply be an open port that empties into a receptacle, or in some embodiments may include a flange or other feature for coupling the sample outlet 128 to a valve or other piping. For example, in at least one embodiment, the outlet 128 may be an opening in the bottom end of the lower shell portion 120, while in other embodiments, the sample outlet 128 may be an opening in the lower end of a sample outlet nozzle 127. As shown in the illustrative embodiments depicted in FIGS. 1-7, the sample outlet nozzle 127 may be, e.g., a frustoconically shaped sample outlet nozzle 127 having a cone half angle of 127a. Furthermore in at least some embodiments, the half angle 127a may be steeper than the half angle 120a of the lower shell portion 120, e.g., by at least approximately 5-10 degrees, so as to facilitate optimal discharge of a fluid sample through the sample outlet 28, as will be further described with respect to FIGS. 14-16 below. For example, in those exemplary embodiments wherein the cone half angle 120a of the lower shell portion 120 is approximately 45 degrees, the half angle 127a of the sample outlet nozzle 127 may be approximately 35-40 degrees or even less, although it should be understood that other half angles 127a may also be used, depending on the overall design parameters of the sampling apparatus 100.

In other illustrative embodiments, e.g., wherein the apparatus 100 is not used to obtain a sample of a fluid flowing through a conduit, the apparatus 100 may not include a sample outlet nozzle 127 and/or a sample outlet 128. Instead, the lower shell 120 may have a substantially flat bottom plate defining the lower boundary of the body 112, similar to the substantially flat top plate 118t defining the upper boundary of the body 112. In such embodiments, the apparatus may be substantially operated so as to function as a flow meter, i.e., a flow measurement apparatus 100, as will be further described below.

Referring back to FIG. 1, it was previously noted that FIG. 1 is a perspective view of the apparatus 100 when viewed from the flow line side, wherein the apparatus 100 has been arranged and oriented in an exemplary operating configuration. In particular, FIG. 1 shows that the flow axis 113 through the body 112 of the apparatus 100 is oriented at a downward flow angle 113a relative to a substantially horizontal direction 123. In this way, the flow of fluid along the flow axis 113 in the flow direction 101 from a conduit (such as the flow line 103 shown in FIG. 18) that is coupled to the fluid inlet 114 and through the apparatus 100 is at least partially gravity assisted. For example, in those illustrative embodiments wherein the fluid flowing into and through the apparatus 100 is, e.g., drilling mud mixed with drill cutting, the flow angle 113a may be in the range of approximately 5-10 degrees, although it should be understood that both larger and smaller flow angles 113a may also be used.

Figure 2:
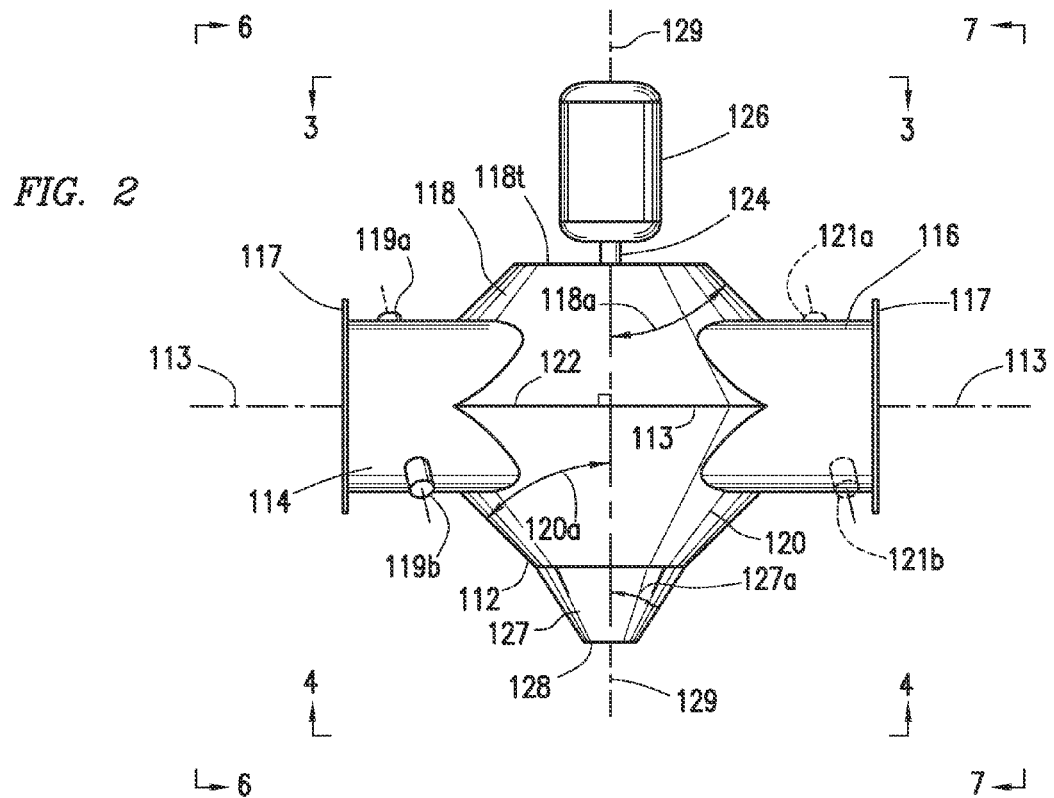
FIG. 2 is a flow line side elevation view of the exemplary fluid sampling and flow measurement apparatus of FIG. 1, wherein, for clarity, the central axis and the flow axis of the illustrative apparatus are arranged vertically and horizontally, respectively.
Figure 3:
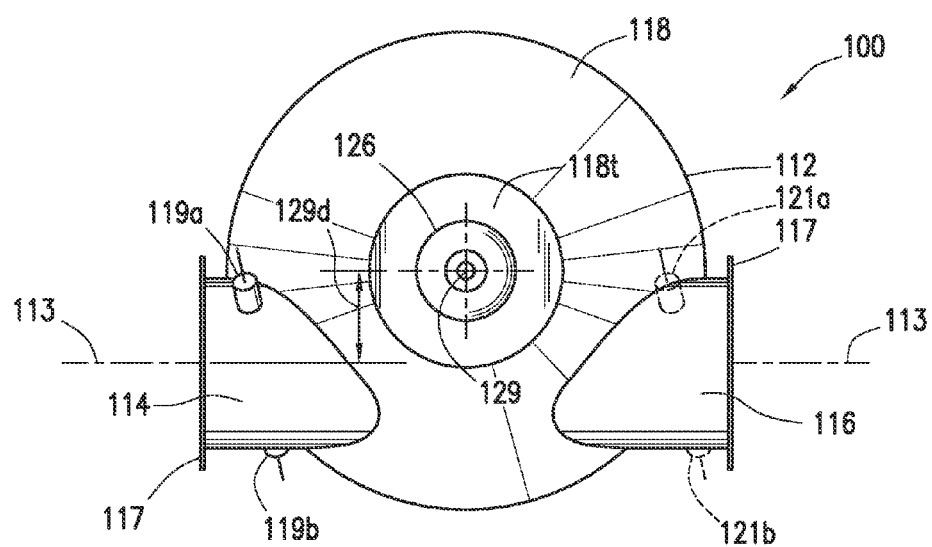
FIG. 3 is a top down plan view of the exemplary fluid sampling and flow measurement apparatus of FIG. 1 taken along the view line "3-3" of FIG. 2.
Figure 4:
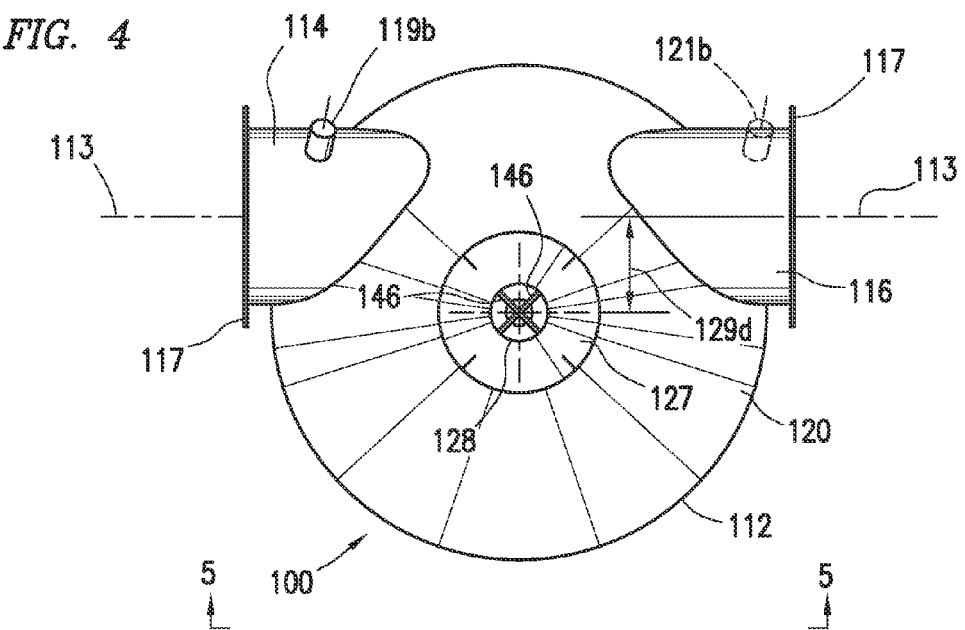
FIG. 4 is a bottom up plan view of the illustrative fluid sampling and flow measurement apparatus of FIG. 1 taken along the view line "4-4" of FIG. 2.

As is shown in FIG. 1, the central axis 129 of the fluid sampling and flow measurement apparatus 100 may be oriented at a sampling angle 129a relative to a substantially vertical direction 125. For additional views and details, see FIGS. 15 and 16 and the associated description set forth below. Furthermore, as illustrated in FIGS. 2 and 5, the central axis 129 may also be substantially perpendicular to the flow axis 113, i.e., such that the axis 129 is rotated about the flow axis 113 by the sampling angle 129a. In certain embodiments, the sampling angle 129a may be established so as to facilitate sweeping or removing a fluid sample from a conduit (such as the flow line 103 shown in FIG. 18) and discharging the fluid sample out of the apparatus 100 through the sample outlet 128, as will be further described with respect to FIGS. 14-16 below. In some illustrative embodiments, the sampling angle 129a may be substantially the same as the half cone angles 118a and 120a. For example, in at least one exemplary embodiment, the half cone angles 118a, 120a and the sampling angle 129a may each be approximately 45 degrees. In such embodiments, the efficiency of the fluid sample sweeping/removal and the fluid sample discharge operations may both be optimized, as will be discussed in conjunction with FIGS. 14-16 below. It should be understood, however, that other sampling angles 129a may also be used, depending on the specific relative configurations of the upper shell portion 118 and the lower shell portion 120 of the body 112.

FIGS. 6 and 7 are inlet and outlet side elevation views, respectively, of the fluid sampling and flow measurement apparatus 100 when viewed substantially along the flow axis 113 through the body 112. As shown in FIG. 6, a blade 134 of a rotating blade assembly 130 partially occludes the flow path of fluid into the fluid inlet 114 and through the apparatus 100 along the flow axis 113. Furthermore, FIG. 6 shows a portion of the inner surfaces 118s and 120s of the upper and lower shell portions 118 and 120, respectively, proximate the edges 134e of the blade 134. Similarly, FIG. 7 also shows a sample chamber inlet blade 134i of the rotating blade assembly 130 partially occluding the flow path through the apparatus along the flow axis 113, as well as the inner surface 118s and 120s proximate the edges 134e of the blade 134i. Additional details of the rotating blade assembly 130 and the operation thereof will be further described below.

Figure 8:
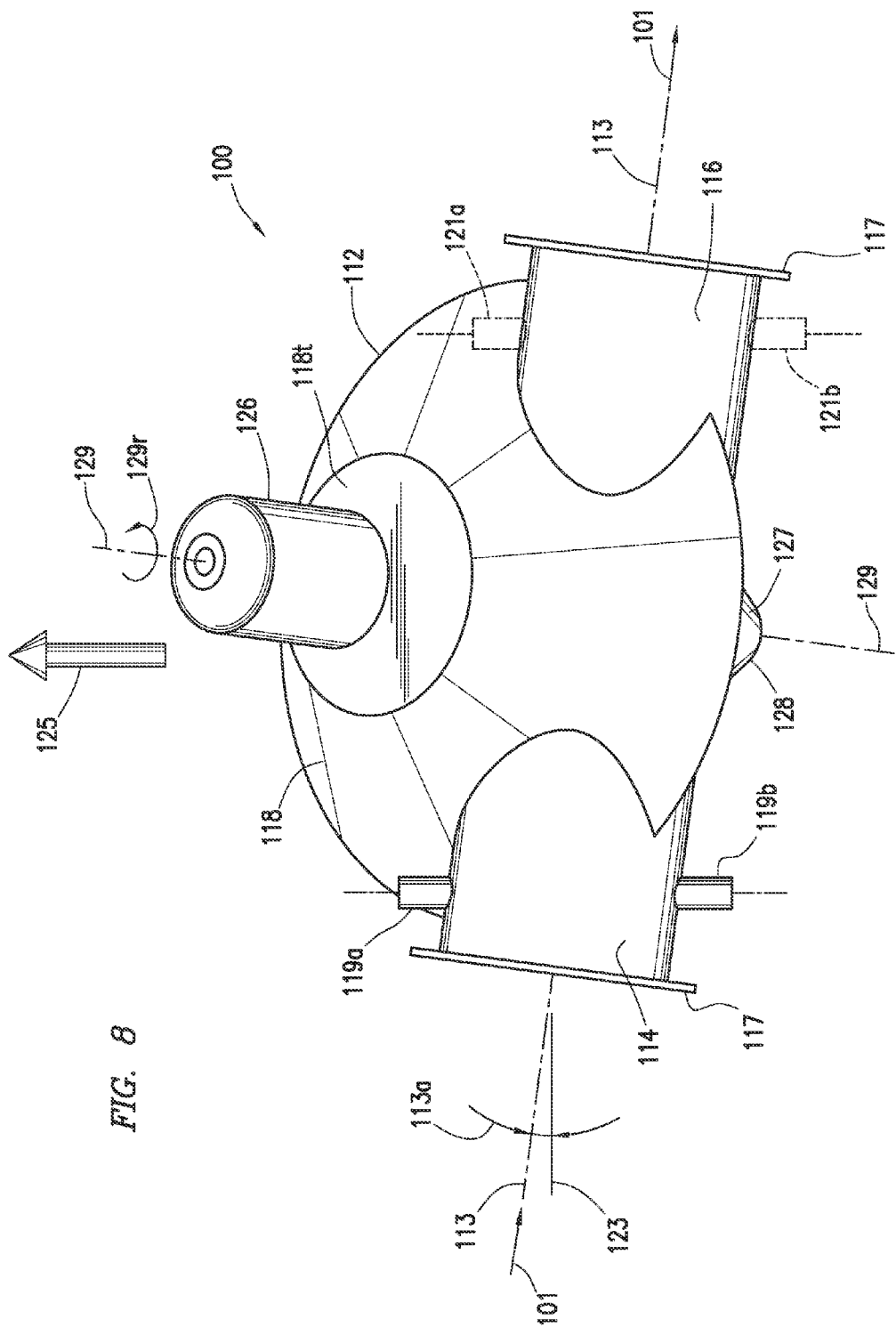
FIG. 8 is a flow line side elevation view of an exemplary fluid sampling and flow measurement apparatus arranged in the illustrative operating orientation depicted in FIG. 1.
Figure 9:
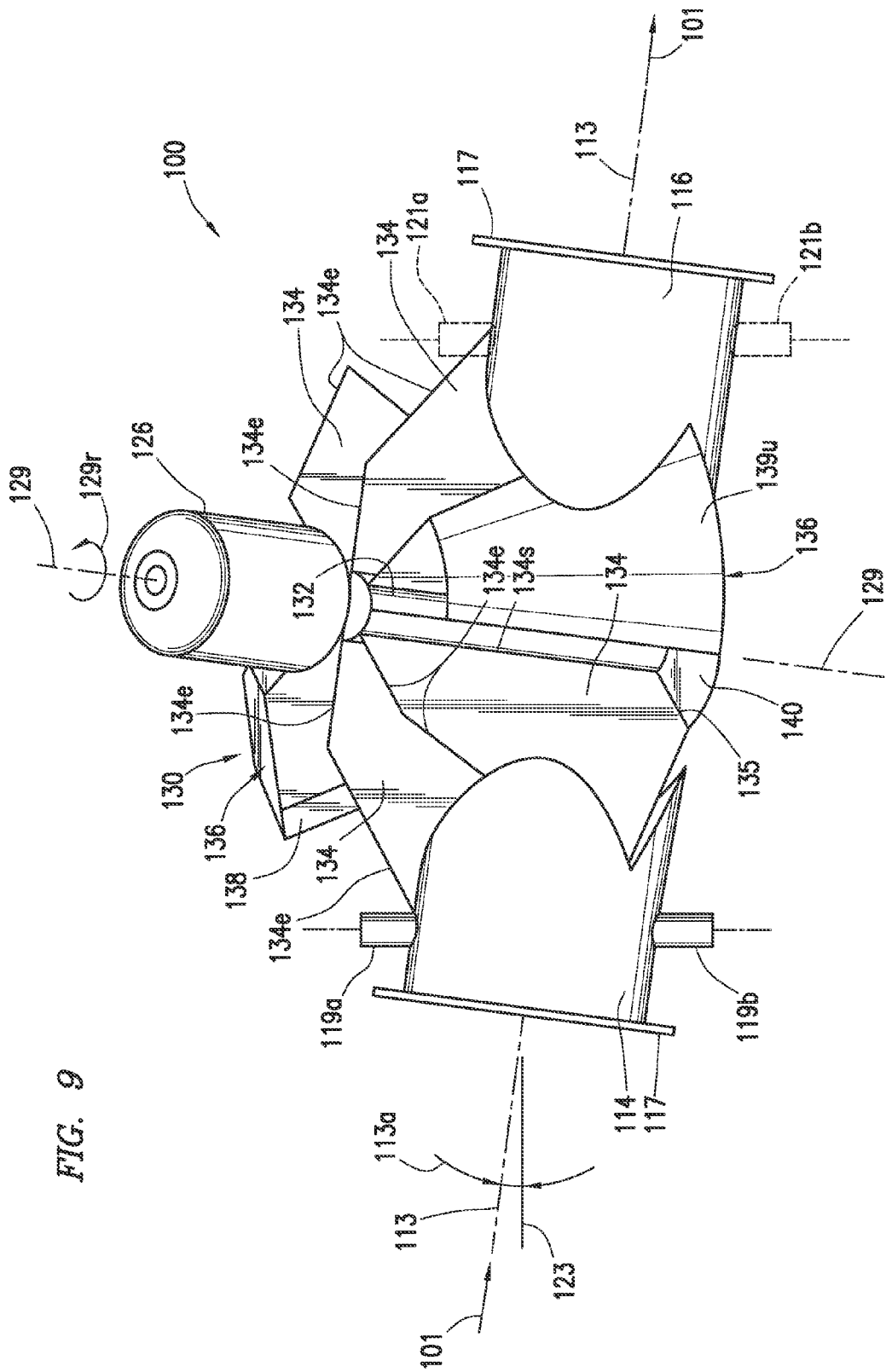
FIG. 9 is a partial cutaway of the flow line side elevation view of the illustrative fluid sampling and flow measurement apparatus shown in FIG. 8 showing one exemplary embodiment of a rotating blade assembly disclosed herein.
Figure 10:
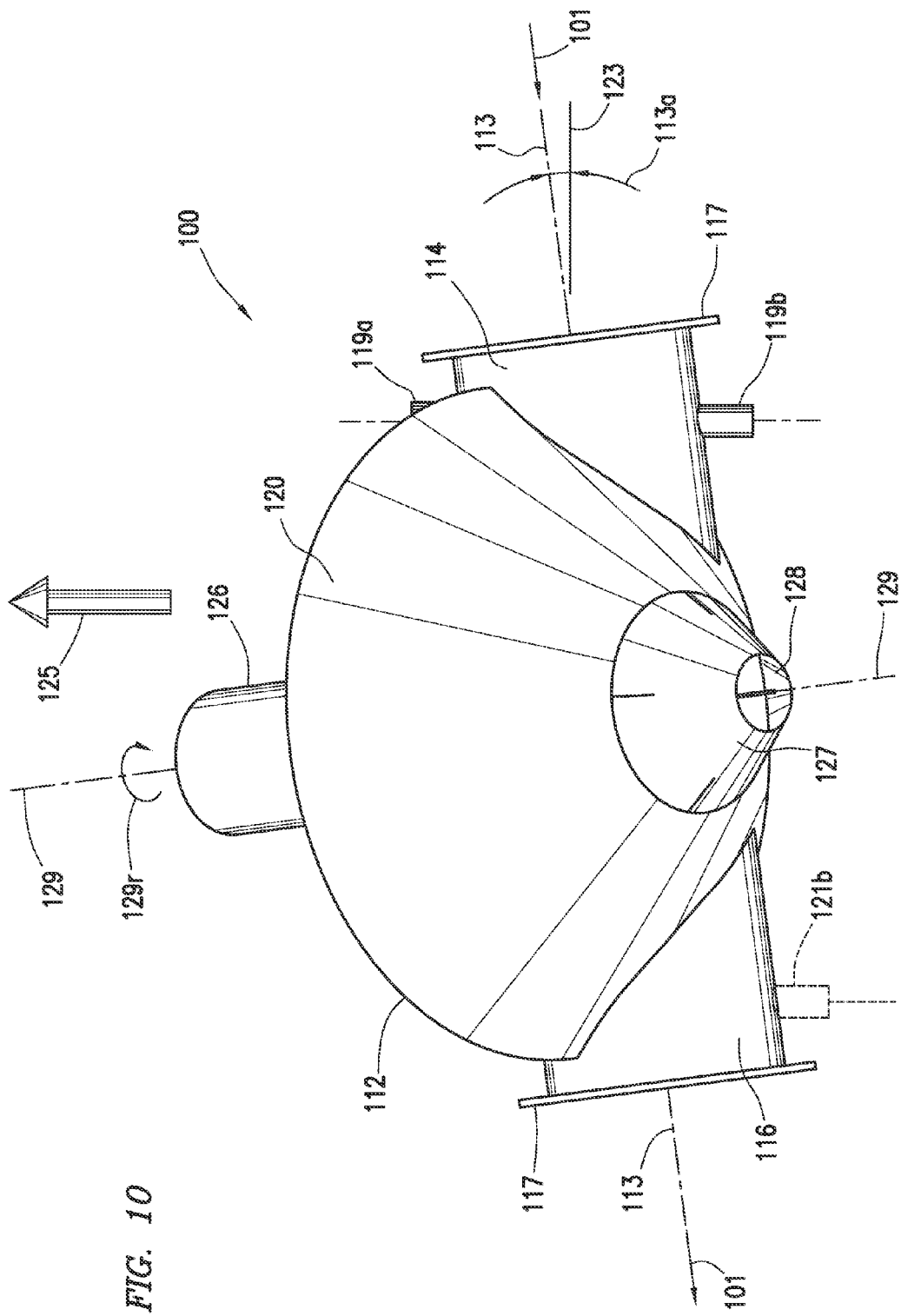
FIG. 10 is the back side elevation view of the illustrative fluid sampling and flow measurement apparatus depicted in FIG. 8.

FIGS. 8-16 are various additional views of the fluid sampling and flow measurement apparatus 100 shown in FIGS. 1-7 above, wherein further details are provided regarding the rotating blade assembly 130 and relationship of the assembly 130 to the body 112 of the apparatus 100, including the fluid inlet 114 and the fluid outlet 116. In particular, FIG. 8 is a side elevation view of apparatus 100 when viewed from the flow line side, or front side, of the apparatus 100, and FIG. 10 is a side elevation view from the back side of the apparatus 100, i.e., opposite of the flow line side. As shown in FIGS. 8 and 10, the illustrative apparatus is arranged and oriented in substantially the same fashion as the apparatus 100 depicted in FIG. 1 and described above, that is, wherein the flow axis 113 is oriented at a downward flow angle 113a relative to the substantially horizontal direction 123, and wherein the central axis 129 is arranged perpendicular to the flow axis 113 and is rotated about the flow axis 113 to an angled orientation relative to the substantially vertical direction 125 by the sampling angle 129a.

Figure 11:
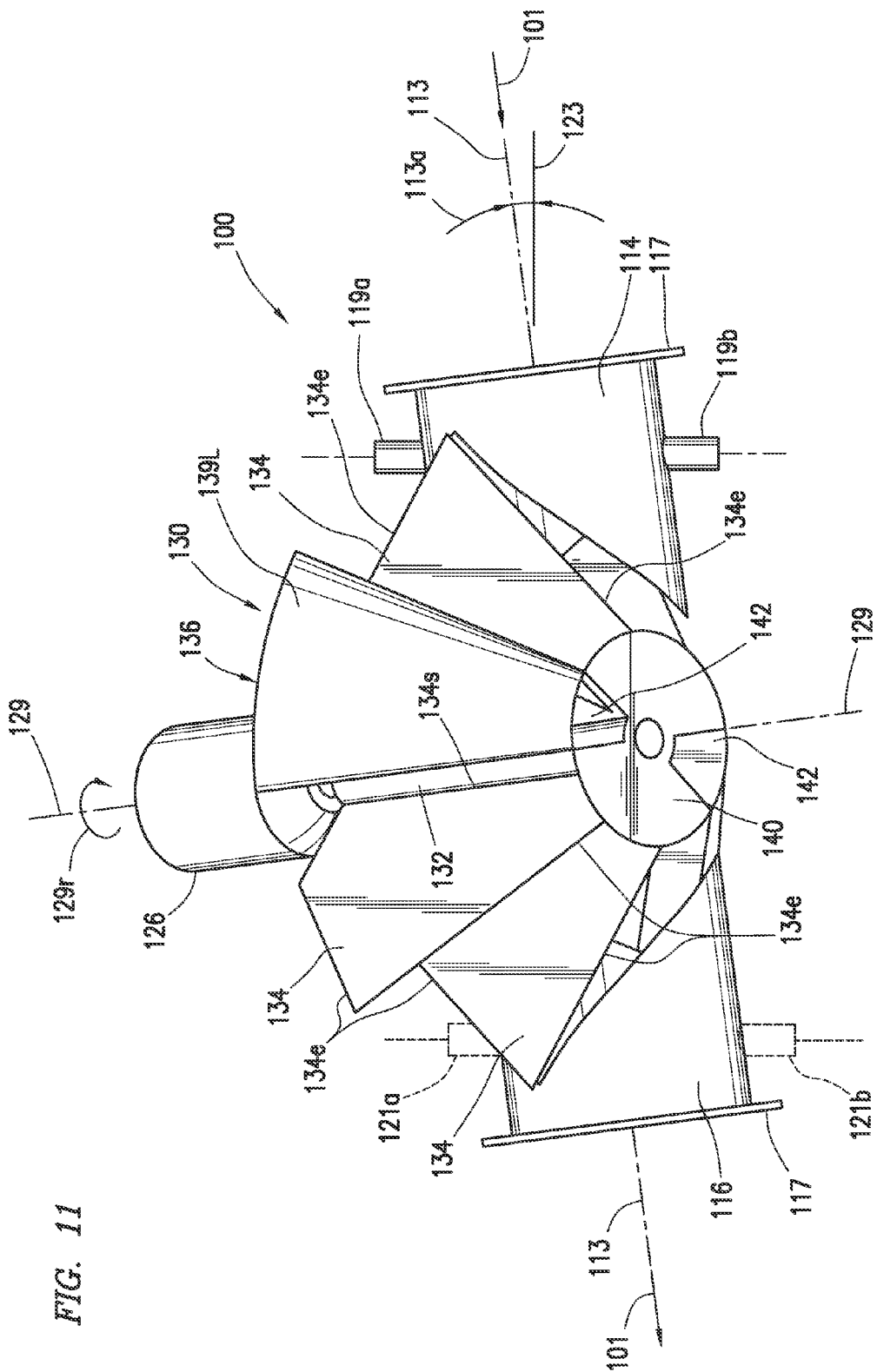
FIG. 11 is a partial cutaway of the back side elevation view of the exemplary fluid sampling and flow measurement apparatus shown in FIG. 10 showing a back side view of the exemplary rotating blade assembly of FIG. 9.
Figure 12:
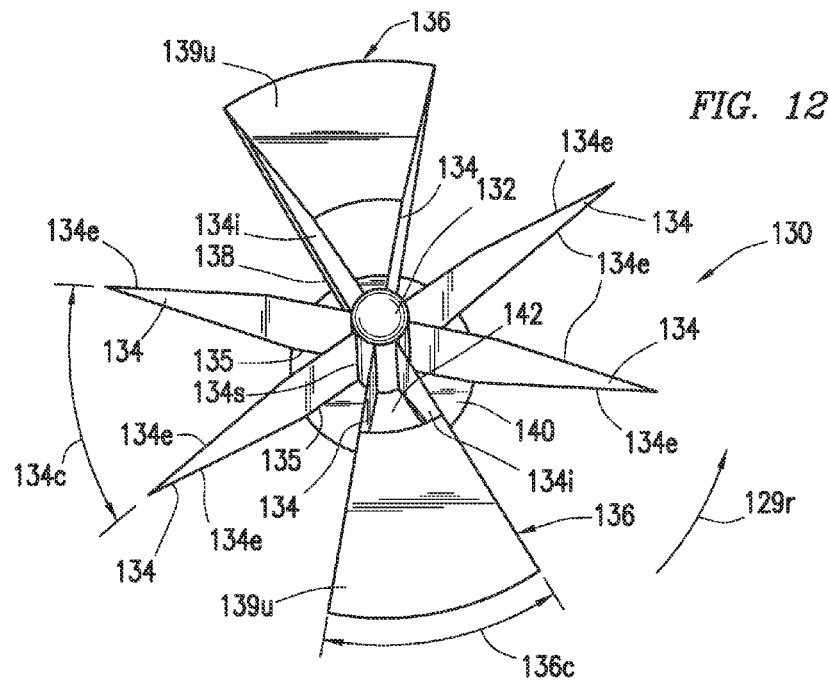
FIG. 12 is a perspective view of the exemplary rotating blade assembly shown in FIGS. 9 and 11 when viewed from above.
Figure 13:
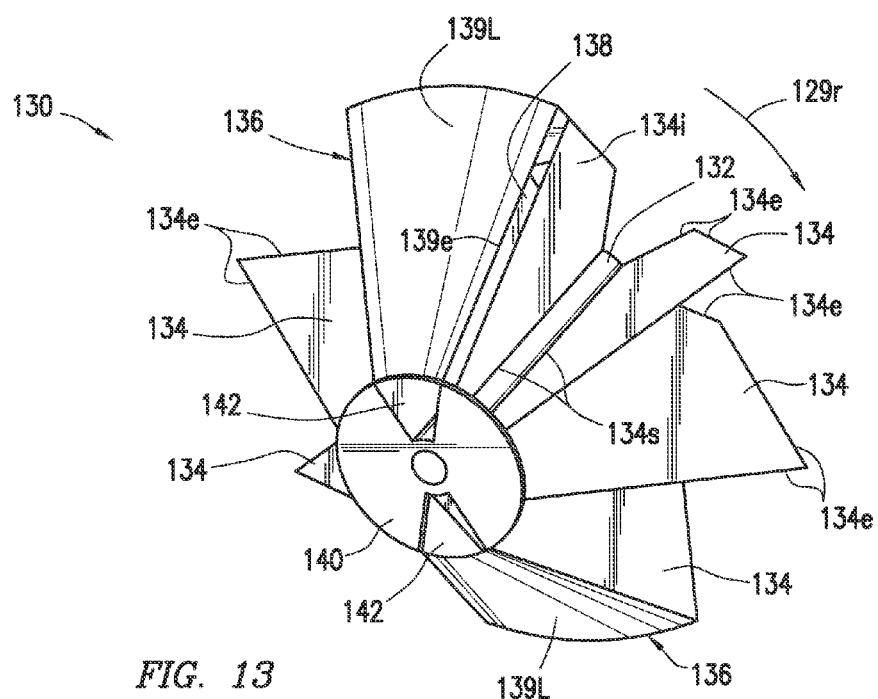
FIG. 13 is a rotated perspective view of the exemplary rotating blade assembly of FIG. 12 when viewed from below.

FIG. 9 is a partial cutaway view of the apparatus 100 shown in FIG. 8 (i.e., when viewed from the same vantage point as in FIG. 8), wherein the upper shell portion 118, the lower shell portion 120, and sample outlet nozzle 127 have been removed so as to reveal and illustrate the rotating blade assembly 130 that is disposed within the body 112. Similarly, FIG. 11 is a partial cutaway view of the apparatus 100 of FIG. 10 (i.e., when viewed from the same vantage point as in FIG. 10), wherein the upper and lower shell portions 118, 120 and the sample outlet nozzle 27 have also been removed to show the rotating blade assembly 130. FIGS. 12 and 13 are additional stand-alone views of the rotating blade assembly 130, i.e., not including any other elements of the apparatus 100, wherein FIG. 12 is a perspective view from above the rotating blade assembly 130 and FIG. 13 is a rotated perspective view from below the assembly 130. Additionally, FIG. 14 is a partial cutaway view of the apparatus 100 shown in FIGS. 8-11 when viewed along the flow axis 113 from the fluid inlet 114 side, wherein, as with FIG. 11, both the upper shell portion 118 and the lower shell portion 120 have been removed to show the rotating blade assembly 130 disposed therein.

Figure 14:
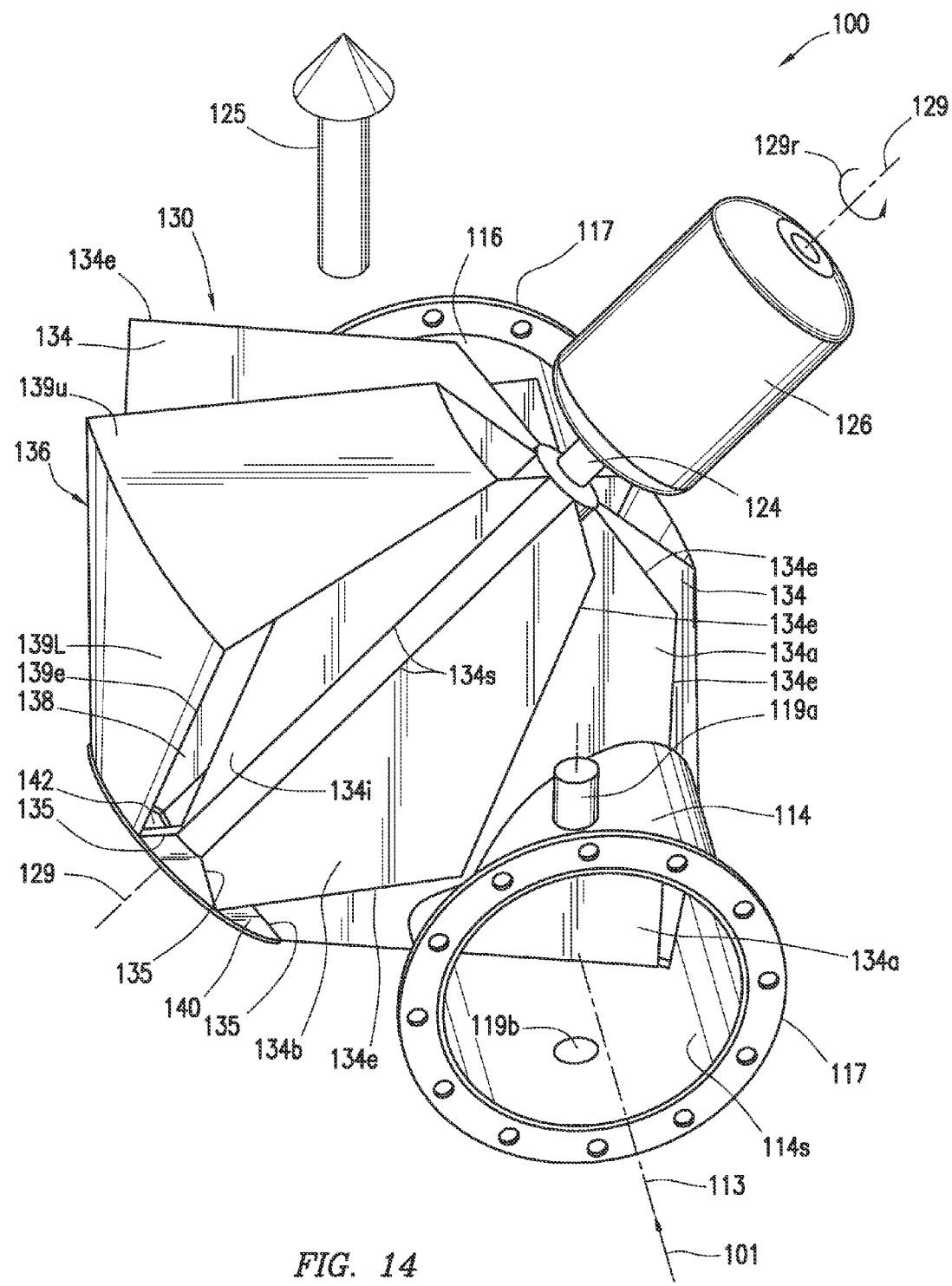
FIG. 14 is a partial cutaway perspective view of the illustrative fluid sampling and flow measurement apparatus of FIG. 8 when viewed from the inlet side showing an exemplary rotating blade assembly.

As shown in the exemplary embodiments depicted in FIGS. 9, 11, and 12-14, the rotating blade assembly 130 may include a center shaft 132, a plurality of blades 134, a plurality of sample chambers 136, and a bottom support disk 140 that is adapted to control fluid communication between the body 112 and the sample outlet nozzle 127 and/or the sample outlet 128 positioned therebelow. In certain embodiments, each blade 134 has an inner edge 134s that is coupled to, and extends substantially radially outward from, the center shaft 132 (see, FIGS. 12-13, described in further detail below). Furthermore, each blade 134 has a lower edge 135 that is coupled to the bottom support disk 140, as shown in FIGS. 9 and 14. Additionally, the blades 134 may have outer and upper edges 134e that are shaped so as to substantially conform to the inner surfaces 118s of the upper shell portion 118 and the top plate 118t, as well as to the inner surfaces 120s of the lower shell portion 120 (see, FIG. 16), so as to substantially reduce, or even prevent, fluid from bypassing the blades 134 during operation of the apparatus 100. Accordingly, as the blade assembly 130 rotates around the center shaft 132, fluid passing through the body 112 from the fluid inlet 114 to the fluid outlet 116 is substantially contained between pairs of adjacent blades 134 and the bottom support disk 140.

For example, in order to reduce and/or prevent fluid bypass, the blades 134 may be sized and configured so as to provide a substantially minimal gap between the edges 134e and the inner surfaces 118s and 120s. In at least some embodiments, the gap between the edges 134e and the inner surfaces 118s and 120s may be approximately ¼" or even less, such as approximately ⅛". Furthermore, in such embodiments, the edges 134e may be hard faced, such as with additional weld-deposited material or tungsten carbide tiles and the like, so as to reduce and/or eliminate inordinate wear of the blades 134 and/or the adjacent inner surfaces 118s and 120s. In other embodiments, such as configurations wherein the gap between the edges 134e and the inner surfaces 118s and 120s may be greater than approximately ¼", flexible wiper material (not shown), such as neoprene or urethane and the like, may be attached along the edges 134e of each blade 134. In such embodiments, the flexible wiper material may thus span the blade edge 134e gap during blade assembly 130 rotation so as to flexibly contact the inner surfaces 118s and 120s, thereby acting to substantially reduce fluid bypass during operation of the fluid sampling and flow measurement apparatus 100, as noted above.

As shown in FIGS. 9, 11, and 12-14, each sample chamber 136 may be defined on either side by a pair of adjacent blades 134 that extend substantially radially outward from the center shaft 132. Additionally, since the inner edge 134s of each blade 134 is coupled to the center shaft 132 and the bottom edge 135 of each blade 134 is coupled to the bottom support disk 140, the inside of each sample chamber may be defined by the shaft 132, and the bottom of each sample chamber may be defined by the disk 140. Furthermore, each sample chamber 136 may be further defined on the outside thereof by respective upper and lower chamber cover plates 136u and 136L, each of which is coupled to the outer edges 134e of the respective pair of blades 134 defining the sides of the chamber 136. In this way, the sample chamber 136 may be at least partially isolated from the fluid that may flow through open spaces between the sides of the chamber 36 and any adjacent blades 134.

In at least some illustrative embodiments, the configuration of the upper chamber cover plate 139u may be adapted to substantially conform to the shape and curvature of the inner surface 118s of the upper shell portion 118, as was previously described with respect to the outer edges 134e of the blades 134. Similarly, the lower chamber cover plate 139L may also be configured so as to substantially conform to the shape and curvature of the inner surface 120s of the lower shell portion 120.

In certain embodiments, each sample chamber 136 may also include a chamber inlet 138 that is adapted to allow a sample portion of the fluid flowing through the sampling apparatus 100 to enter the chamber 136 and a chamber outlet 142 that is adapted to discharge the sample portion out of the chamber 136 and through the sample outlet 128. In some embodiments, the chamber inlet 138 may be positioned on the leading side of the sample chamber 136—that is, on the front side of the chamber 136 in the direction of blade assembly 130 rotation and fluid flow through the apparatus 100 (as described in further detail below)—and may have any size, shape, and configuration that may be necessary to allow the desired volume of fluid to enter the sample chamber 136.

Figure 16:
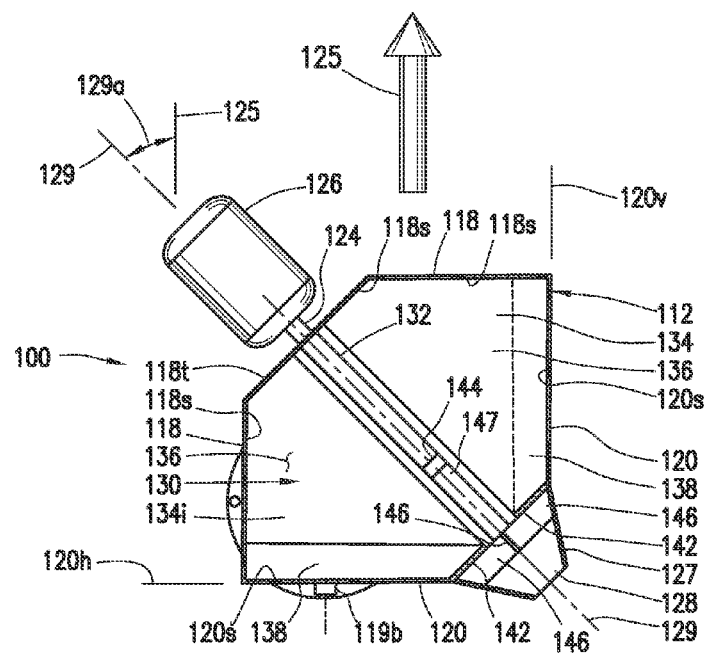
FIG. 16 is a partial sectional view of a the exemplary fluid sampling and flow measurement apparatus of FIG. 15.

For example, as shown in the exemplary embodiment of the rotating blade assembly 130 depicted in FIGS. 9, 11, and 12-14, the chamber inlet 138 may be defined by an opening in the blade 134 that is positioned on the leading side of the sample chamber 136. Furthermore, the opening/chamber inlet 138 may be proximate a leading edge 139e of the lower chamber cover plate 139L, thus enabling that the inlet 138 to sweep through the fluid as it flows through the apparatus 100 along the flow axis 113. In such embodiments, the leading blade 134 of the chamber 136 may be, for example, a modified chamber inlet blade 134i that is configured substantially similar to each of the other blades 134, wherein however the inlet blade 134i may be trimmed, cut, and/or otherwise modified to include the opening chamber inlet 138. In one embodiment, the chamber inlet 138 may be defined by a single opening having a substantially rectangular shape that extends for at least a part of, or even substantially the entirety of, the length of the leading edge 139e, as shown in FIGS. 13, 14, and 16. In other embodiments, the chamber inlet 138 may be defined by a plurality of spaced apart openings having any desired shape, e.g., square and/or rectangular. Furthermore, the plurality of spaced apart openings may have either a regular or irregular spacing, as may be required for the specific application.

The chamber outlet 142 may be disposed at the bottom of the sample chamber 136, as shown in FIGS. 11-13, and may be adapted to provide a flow passage for the fluid sample to move from the sample chamber 136 and through the bottom support disk 140 to the sample outlet 128. For example, in certain embodiments, the chamber outlet 142 may be an opening in the bottom support disk 140 that is substantially defined on either side by the pair of blades 134 (or blade 134 and inlet blade 134i) that form the sides of the sample chamber 136, the center shaft 132 that defines the inside of the chamber 136, and the lower chamber cover plate 139L that defines the bottom outside of the chamber 136. It should be understood that chamber outlet 142 may also be defined by a plurality of smaller openings, as may be required to optimally discharge the desired sample size to the sample outlet 128.

Referring now to FIGS. 12 and 13, the illustrative rotating blade assembly 130 depicted therein includes, for example, eight blades 134 and two sample chambers 136. However, it should be understood by those of ordinary skill after a complete reading of the present disclosure that any of the illustrative rotating blade assemblies 130 described herein may include either a fewer number of blades 136, e.g., two to seven, or a greater number of blades 136, e.g., nine or more, depending on the overall design and operating parameters of a given fluid sampling and flow measurement apparatus 100. Similarly, any rotating blade assembly 130 in accordance with the presently disclosed subject matter may have a fewer number of sample chambers 136, e.g., one, or a greater number of sample chambers 136, e.g., three or more.

In at least one exemplary embodiment, each of the plurality of blades 134, including the blades 134 and/or chamber inlet blades 134i that define the sides of the sample chambers 136, may have a substantially equal angular spacing. In other words, the angular spacing 136c between the blades 134 and/or 134i that define the sides of the sample chambers 136 may be substantially the same as the angular spacing 134c between each of the remaining blades 134. However, in other embodiments, the angular spacing 136c may be greater than or less than the angular spacing 134c, depending on the design and operating parameters of the sampling apparatus 100, such as the characteristics of the fluid flowing through the apparatus 100, and the like. For example, the angular spacing 136c between the blades 134 and/or 134i that define the sides of the sample chambers 136 may be established based on the required volumetric size of the fluid sample obtained from the apparatus 100 during operation, e.g., a smaller angular spacing 136c for smaller sample sizes and a larger angular spacing 136c for larger sample sizes.

In other exemplary embodiments, the angular spacing 134c may not be uniform between each adjacent pair of blades 134, but instead may be adjusted based on other design parameters of the apparatus 100, such as the proximity of a given blade 134 to a given sample chamber 136. Similarly, in those illustrative embodiments wherein two or more sample chambers 136 are included in the rotating blade assembly 130, the angular spacing 136c between the blades 134 and/or 134i defining each given sample chamber 136—and the corresponding the size of that sample chamber 136—may also be different, as required.

In various embodiments of the present disclosure, the center shaft 132 may be coupled to the rotatable shaft 124 (see, FIGS. 1-7 described above), thereby allowing the rotating blade assembly 130 to be rotated by the drive motor 126. Furthermore, the drive motor 126 is adapted to rotate the rotating blade assembly 130 such that the blades 134 and any sample chambers 136 sweep along the flow axis 113 in substantially in the same direction as the fluid flow direction 101 (see, FIGS. 1 and 18) through the apparatus 100. Accordingly, the rotational direction 129r of the rotating blade assembly 130 is counterclockwise (see, FIGS. 8, 12, and 14) when viewed from above and the apparatus 100 and along the central axis 129, and clockwise (see, FIGS. 10, 13, and 13) when viewed from below and the apparatus 100 and along the central axis 129.

As can be seen in FIGS. 9, 11, and 12-14, and as was previously noted with respect to FIGS. 6 and 7 above, the rotation of the rotating blade assembly 130 may periodically restrict, or at least partially occlude, fluid communication between the fluid inlet 114 and the fluid outlet 116. This occurs as the rotating blades 134 and/or sample chambers 136 sweep through the flow axis 113 that runs through the body 112, thus at least partially blocking the flow of fluid through the apparatus 100. Similarly, the rotation of the blade assembly 130 may also periodically place the sample chamber 136 in fluid communication with the fluid inlet 114 via the sample chamber inlet 138, based upon the angular velocity of blade assembly 130, as will be further described below.

For example, as is shown FIG. 14, which is a partial cutaway perspective view of the apparatus 100 with the upper and lower shell portions 118 and 120 removed so as to show the rotating blade assembly 130, a first blade 134a can be seen through the fluid inlet 114, where it is positioned at an angle across the flow axis 113. As the rotating blade assembly 130 is continuously rotated in the direction 129r (i.e., counterclockwise when viewed from above) so that first blade 134a moves substantially along the fluid flow direction 101, the first blade 134a continuously sweeps across the flow axis 113, thus at least partially occluding flow through the apparatus 100, depending on the specific position of the first blade 134a relative to the inside surfaces 114s of the fluid inlet 114 and the inside surfaces 118s and 120s of the upper and lower shell portions 118 and 120.

In certain embodiments, the flow restriction created by the first blade 134a on the fluid flowing through the apparatus 100 gradually increases as the first blade 134a sweeps across the flow axis 113 and reaches its greatest at the point where the first blade 134a is substantially perpendicular to the flow axis 113. After the first blade 134a rotates beyond the perpendicular point relative to the flow axis 113, the flow restriction through the apparatus 100 cause by the first blade 134a gradually decreases until the first blade 134a sweeps out of the flow window between the fluid inlet 114 and the fluid outlet 116. However, as the rotating blade assembly 130 continues to rotate around the central axis 129, a second blade 134b rotates into position behind the first blade 134a and acts to gradually increase and then gradually decrease the flow restriction through the apparatus 100 in similar fashion to the first blade 134a as described above.

As is shown FIG. 14, a sample chamber 136 is positioned behind and adjacent to the second blade 134b. Therefore, as the rotating blade assembly 130 is rotated by the drive motor 126, the sample chamber 136 would therefore follow the second blade 134b into the flow axis 113. As such, the chamber inlet 138 of sample chamber 136 will periodically be in fluid communication with the fluid inlet 114 based upon the angular velocity of the blade assembly 130, thus allowing at least a portion of the fluid flowing into the apparatus 100 through the fluid inlet 114 to flow into the sample chamber 136 through chamber inlet 138. Thereafter, the fluid that is received by the sample chamber 136 may be discharged from the sample chamber 136 through the chamber outlet 142, as will be further described with respect to FIGS. 15 and 16 below. As noted previously, in at least some illustrative embodiments, the bottom support disk 140 may be positioned over the sample nozzle outlet 127 and the sample outlet 128 so that only the sample portion of the fluid flowing through the apparatus 100 that is collected in the sample chamber 136 is permitted to pass through the chamber outlet 142 and to flow out of the apparatus 100 through the sample outlet 128. Thus, the remaining fluid that is flowing through the apparatus 100 between the various blades 134 (i.e., except the blades 134 and/or 134i defining the sides of the sample chamber 136) is substantially prevented from flowing out of the sample outlet 128 by the bottom support disk 140.

Therefore, in certain illustrative embodiments, the rotating blade assembly 130 may be adapted to separate a controlled volume of fluid, i.e., sample portion, from the flow of fluid through a conduit, e.g., the flow line 103 shown in FIG. 18, and to divert the sample portion of fluid out of the sampling apparatus 100 through the sample outlet 128. Furthermore, since the sample outlet 128 may be substantially aligned with the central axis 129 of the body 112 that is substantially perpendicular to the flow axis 113 of the flow line 103 (FIG. 18), a sample may be automatically obtained, e.g., without the direct manual interaction of personnel, from the sample outlet 128 of the apparatus 100 with minimal splash and substantially without interrupting the flow of fluid through the flow line 103.

Figure 15:
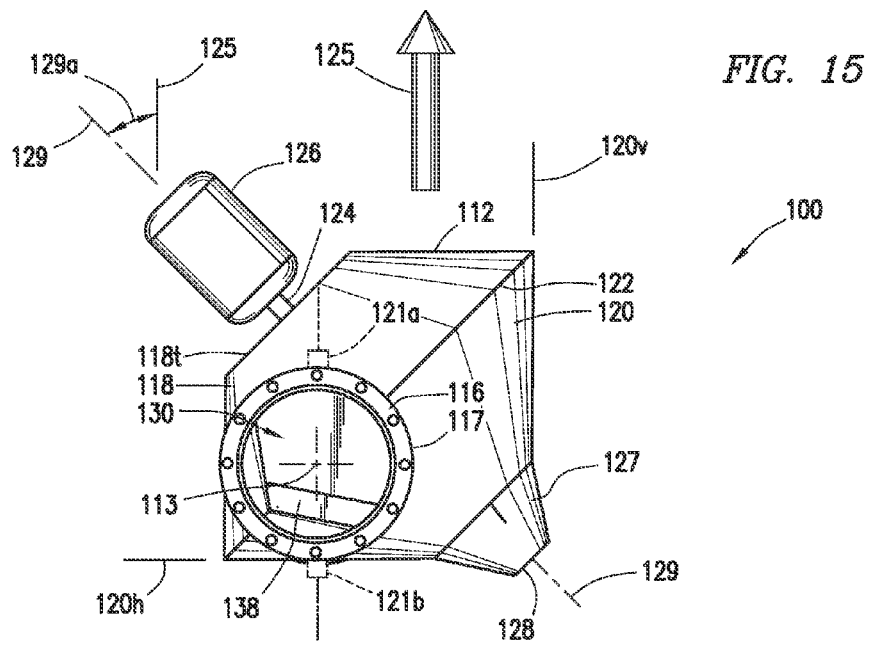
FIG. 15 is an outlet side elevation view of the illustrative fluid sampling and flow measurement apparatus of FIG. 8 when viewed along the flow axis.

FIG. 15 is an outlet side elevation view of the fluid sampling and flow measurement apparatus 100 shown in FIGS. 8-14 when viewed substantially along the flow axis 113, and FIG. 16 is a partial sectional view of the apparatus 100 illustrated in FIG. 15. In the exemplary embodiments depicted in FIGS. 15 and 16, the fluid sampling and flow measurement apparatus 100 is arranged and oriented in the exemplary operation orientation shown in FIGS. 8-10, such that the central axis 129 of the apparatus 100 is substantially perpendicular to the flow axis 113 and is rotated about the flow axis 113 to an angled orientation relative to the substantially vertical direction 125 by the sampling angle 129a, as was previously noted with respect to FIGS. 1-7 above. For example, as shown in FIGS. 15 and 16, the central axis 129 may be oriented at a sampling angle 129a of about 45 degrees, and the half angles 118a, 120a of the upper and lower shell portions 118, 120 (see, FIGS. 2-6) may also be approximately 45 degrees. In such embodiments, one side 120h of the lower shell portion 120 may be oriented along a substantially horizontal plane, and the opposite side 120v of the lower shell portion 120 may be oriented along a substantially vertical plane, as indicated in FIGS. 15 and 16.

During operation of the fluid sampling and flow measurement apparatus 100, the rotating blade assembly 130 is rotated by the drive motor 126 so as to bring chamber inlet 138 adjacent to the substantially horizontally oriented side 120h of the lower shell portion 120, that is, at or near the bottom of the body 112 when the apparatus 100 is oriented at the sampling angle 129a, as shown in FIG. 16. As the sample chamber 136 is rotated and positioned so that the chamber inlet 138 is adjacent to the bottom of the body 112, a portion of the fluid that is flowing through the fluid inlet 114 may then flow into the sample chamber 136 through the chamber inlet 138. Furthermore, in this orientation, the sample chamber 136 is positioned substantially above the horizontally oriented side 120h of the lower shell 120 and substantially laterally adjacent to the sample outlet nozzle 127 and the sample outlet 128.

As the rotating blade assembly 130 continues to rotate, the sample chamber 136 may then be rotated up and away from its position adjacent to the substantially horizontal side 120h of the lower shell portion 120 at the bottom of the body 112. Furthermore, during this sample chamber 136 upward rotation, a gravity-assisted discharge of the fluid sample commences through the chamber outlet 142, into the sample outlet nozzle 127, and out of the apparatus through the sample outlet 128. Eventually, the sample chamber 136 is rotated upward until the chamber inlet is adjacent to the substantially vertically oriented side 120v of the lower shell portion 120 and the sample chamber is positioned substantially above the sample outlet nozzle 127 and the sample outlet 128. With the sample chamber 136 in this position adjacent to the vertically oriented side and above the sample outlet 128, the gravity-assisted discharge of the sample fluid portion from the sample chamber 136 through sample outlet 128 may be substantially maximized.

As is further illustrated in FIG. 16, the rotating blade assembly 130 may be supported by a bearing 144, which, in certain embodiments, may be coupled to the end of a support shaft 147. Furthermore, the support shaft 147 may be mounted to one or more support arms 146 that are coupled to the body 112, e.g., inside of the sample outlet nozzle 127, and positioned above the sample outlet 128. In at least some embodiments, the support shaft 147 may extend upward from the support arms 146 and into the center shaft 132 of blade assembly 130, thus substantially isolating the bearing 144 from fluids flowing through the apparatus 10 and/or out of the sample outlet 128.

Figure 17:
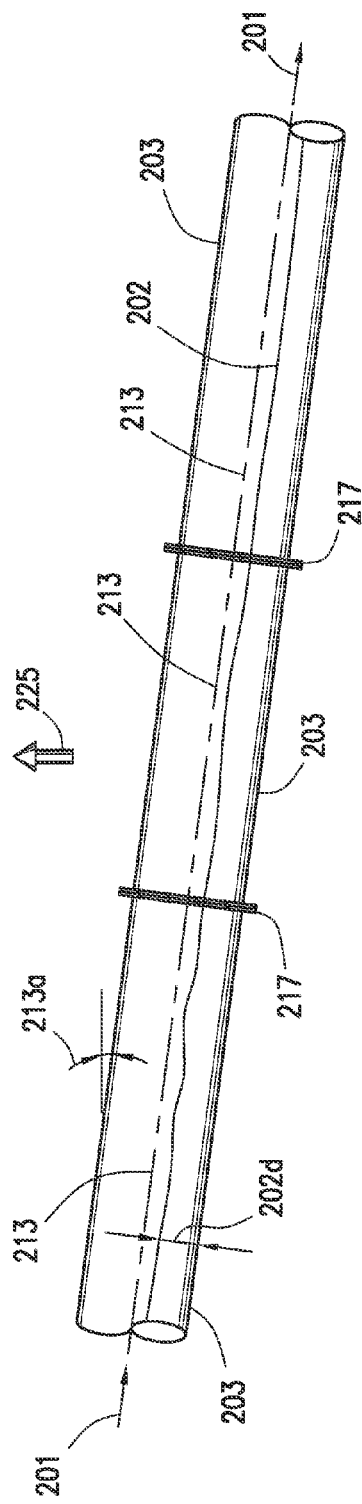
FIG. 17 is a side elevation view of an illustrative prior art flow line when arranged in a typical operating orientation.

FIG. 17 is a side elevation view of an illustrative prior art flow line 203 that is arranged in a typical operating orientation and may be part of an overall fluid circulation system that is used for flowing a fluid 202, such as drilling fluid 202 and the like, between various pieces of equipment at a drilling rig site, such as from a wellhead (not shown) to a separation system (not shown). As shown in FIG. 17, the flow line 203 is oriented at a downward angle 213a relative to a substantially horizontal plane so as to facilitate a gravity-assisted flow of the drilling fluid through the flow line 203 along the flow direction 201. In some applications, the flow line 203 can be substantially continuous, that is, without any mechanical connections, whereas in other applications the flow line 203 can include one or more sections or spool pieces 203 that are connected together using couplings 217, such as flanges and the like, as shown in FIG. 17. Furthermore, when coupled together, the centerlines 213 of the various sections or spool pieces 203 are substantially aligned so as to facilitate a substantially continuous and relatively smooth flow 201 of drilling fluid 202 through the assembled flow line 203.

In many drilling fluid circulation systems, the flow line 203 is generally not completely full of the drilling fluid 202, as may normally be the case when liquids that are pumped through a flow line under high pressures. Instead, under the gravity-assisted flow regime that is commonly used to circulate drilling fluids, the depth 202d of the drilling fluid 202 as it flows through the flow line 203 may only be between approximately ⅓ to ½ of the flow line diameter, and the remaining volume of the flow line 203 is substantially ambient pressure.

FIG. 18 is a side elevation view of one exemplary embodiment of a fluid sampling and flow measurement apparatus 100 of the present disclosure when arranged in an illustrative flow line 103. As shown in FIG. 18, the apparatus 100 may be installed into the flow line 103 as a "spool piece" such that the flow axis 113 running through the apparatus 100 from the fluid inlet 114 to the fluid outlet 116 is substantially aligned with the central flow axis 103x of the flow line 103. In certain embodiments, the fluid sampling and flow measurement apparatus 100 may be installed in the flow line 103 by connecting the couplings 117 on the fluid inlet 114 and outlet 116 to corresponding mating couplings 117m on the flow line 103, thus facilitating the relatively easy removal of the apparatus 100 from the flow line 103 for maintenance or replacement. Furthermore, in at least one embodiment, a bypass spool with appropriate valving and connections (not shown) may also be installed to the flow line 103 in such a manner that the apparatus 100 may be isolated from the flow 101 of fluid 102, e.g., drilling fluid 102. In this way, the flow 101 of drilling fluid 102 may be routed so as to bypass the apparatus 100, thus permitting a substantially continuous flow 101 of the fluid 102 through the flow line 103 without requiring a temporary shutdown of the overall fluid circulation system (not shown).

As noted above with respect to FIGS. 8-16, the rotating blade assembly 130 disposed inside of the body 112 of the flow measurement apparatus 100 may be adapted to be rotated by the drive motor 126 such that the blades 134 and sample chambers 136 sweep along the flow axis 113 in substantially in the same direction as the fluid flow direction 101 through the apparatus 100. The rotating blade assembly 130 may therefore be rotated under only three different angular velocity regimes relative to the flow speed of the drilling fluid 102 as it flows through the flow line 103 and the apparatus 100, as will be further described below.

In a first case, the angular velocity of the rotating blade assembly 130 may be such that the blades 134 and sample chambers 136 sweep along the flow axis 113 at a speed that is less than the flow speed of the drilling fluid 102 through the flow line 103. As noted with respect to the prior art flow line system 203 depicted in FIG. 17, the drilling fluid 202 typically does not completely fill the flow line 203 as it is flowing therethrough. Instead, the fluid 202 flow through the flow line 203 with a depth 202d (or fluid level 202d) that is most often in the range of ⅓ to ½ of the flow line diameter (see, FIG. 17). Accordingly, in those embodiments wherein the rotating blade assembly is operated at an angular velocity that is less than the flow speed of the drilling fluid 102 through the flow line 103, the blocking action of the relatively slower moving blades 134 and/or sample chambers 136 may act to create a greater restriction or occlusion of the flow 101 of drilling fluid 102 through the apparatus 100, in the manner previously described with respect to FIGS. 8-16 above. In such cases, the depth (i.e., level) of the flow 101 of drilling fluid 102 inside of the flow line 103 upstream of the apparatus 100 may tend to increase over time as the drilling fluid 102 backs up behind the apparatus 100. Commensurately, the depth of the drilling fluid 102 moving downstream of the apparatus 100 may tend to decrease time, and will generally be less that the upstream depth.

In a second case, the angular velocity of the rotating blade assembly 130 may be such that the blades 134 and sample chambers 136 sweep along the flow axis 113 at a speed that is greater than the flow speed of the drilling fluid 102 through the flow line 103. In such cases, the sweeping action of the relatively faster moving blades 134 and/or sample chambers 136 may act to "pump" the drilling fluid downstream of the flow measurement apparatus 100, such as in a manner that is similar to, for example, a centrifugal pump and the like. Therefore, the depth (i.e., level) of the flow 101 of drilling fluid 102 entering the apparatus 100 from upstream may tend to decrease over time as the drilling fluid 102 is swept, or "pumped," downstream. Furthermore, the downstream depth of the flow 101 of drilling fluid 102 may also decrease over time, and will generally be greater than the upstream depth.

Finally, in a third case, the angular velocity of the rotating blade assembly 130 may be such that the blades 134 and sample chambers 136 sweep along the flow axis 113 at a speed that is substantially the same as the flow speed of the drilling fluid 102 through the flow line 103. In such cases, the depth (i.e., level) of the flow 101 of drilling fluid 102 inside of the flow line 103 that is entering the flow measurement apparatus 100 from upstream may tend to remain substantially constant over time, since the rotating blade assembly 130 is being operated to allow the drilling fluid 102 to move through the apparatus 100 at a substantially constant speed, i.e., with minimal flow restriction. Additionally, the depth of the flow 101 of drilling fluid 102 downstream of the apparatus 100 may also remain substantially constant, and furthermore may also be substantially the same as the upstream depth.

In view of the above-described three different relative angular velocity regimes under which the rotating blade assembly 130 may be operated, it should be understood by those of ordinary skill in art after a complete reading of the present disclosure that, in those embodiments wherein the rotating blade assembly 130 is rotated at an angular velocity such that the depth (i.e., level) of the flow 101 of drilling fluid 102 upstream of the apparatus 100 is substantially constant, then the angular velocity of the rotating blade assembly 130 can be considered to be substantially directly proportional to the flow speed of the drilling fluid 102 through the flow line 103 and the apparatus 100. Furthermore, since the geometry (i.e., the inside diameter) of the flow line 103 is known, the volumetric flow rate of the drilling fluid 102 flowing through the flow line 103 may be quantitatively determined based upon the angular velocity of the rotating blade assembly 130 and the actual depth of the drilling fluid 102 inside of the flow line 103 and upstream of the apparatus 100. In this way, the apparatus 100 may be operated to substantially function as a flow meter, i.e., a flow measurement apparatus 100.

Various illustrative methods that may be used to operate the apparatus 100 as a flow meter will now be described in conjunction with FIG. 18. As described above with respect to FIGS. 1-7, one or more sensors 119a/b, which may be, for example, level sensors, pressure sensors, capacitance sensors, ultrasonic transceivers, and the like, may be installed on the fluid inlet 114, or at some other appropriate location upstream of the apparatus 100. Furthermore, the sensors 119a/b (and/or the sensors 120a/b, as required) may be adapted to obtain relevant data, e.g., pressure and/or fluid level, on the drilling fluid 102 as it flows past the sensors 119a/b. In certain embodiments, the sensors 119a/b (and/or 120a/b) may be operatively coupled to a control system 106 (schematically illustrated in FIG. 18), which may in turn be operatively coupled to the drive motor 126.

In operation, the sensor data obtained by one or more of the sensors 119a/b (and/or the sensors 120a/b) on the drilling fluid 102 as is flows into and/or out of the apparatus 100 may be used by the control system 106 to control the operation of the drive motor 126 based on the specific desired operating regime. For example, in those illustrative embodiments wherein external changes to the drilling conditions may cause the flow rate in the flow line 103 upstream of apparatus 100 to decrease, the sensors 119a/b will operate to obtain data relevant to the decreased flow and transmit the obtained data to the control system 106. Based on the data transmitted by the sensors 119a/b, the control system 106 will respond to increase the depth (i.e., level) of drilling fluid 102 upstream of the apparatus 100 by controlling the drive motor 126 so as to reduce the angular velocity of the rotating blade assembly 130, which may thus create a greater flow restriction through the apparatus 100, thereby increasing the depth of the flow 101 of drilling fluid 102 upstream of the apparatus 100.

Similarly, when changes in the drilling conditions cause the flow rate of the returned drilling fluid flowing through the flow line 103 to increase, the sensors 119a/b will operate to detect an increase in fluid level upstream of the apparatus 100, and the control system 106 will respond to the increased level data detected by the sensors 119a/b by controlling the drive motor 126 so as to increase the angular velocity of the rotating blade assembly 130. In other words, the control system 106 may use relevant sensor data obtained by the sensors 119a/b (and or 120a/b) to control the drive motor 126 such that the angular velocity of the rotating blade assembly 130 is either periodically or substantially continuously adjusted up and/or down as the fluid flow through the flow line 103 changes with changing drilling conditions so that the depth (i.e., level) of the drilling fluid 102 upstream of the apparatus 100 remains substantially constant. In this way, the angular velocity of the rotating blade assembly 130 will be directly proportional to the flow rate of fluid in the partially filled flow line 103.

In at least one illustrative operating regime of the apparatus 100, the depth 102a of the drilling fluid 102 flowing through the flow line 103 to the apparatus 100 may initially be substantially the same as the fluid depth 202d of the drilling fluid 202 flowing through the prior art system of FIG. 17, that is, on the order of approximately ⅓ to ½ of the flow line diameter. During the early stages of the fluid flow 101 through the flow line 103, the control system 106 may be used to control operation of the drive motor 126 in the manner previously described, i.e., by adjusting an angular velocity of the rotating blade assembly 130 such that it is less than the flow speed of the drilling fluid 102. In this way, a degree of back pressure may be created on the apparatus 100 as the flow 101 of drilling fluid 102 through the apparatus 100 may be restricted as set forth above. In this way, the depth of the drilling fluid 102 in the flow line 103 immediately upstream of the apparatus 100 may be increased to a depth 102b, as shown in FIG. 18. In certain embodiments, the depth 102b be approximately ½ to ⅔ of the flow line diameter, although different depths 102b may also be used depending on the desired operational regime of the apparatus 100.

In at least one embodiment, the control system 106 may be used to initially reduce the angular velocity of the rotating blade assembly 130 for only a limited amount of time, such that a pool 104 of drilling fluid 102 is formed upstream of the apparatus 100, that extends for a distance 105 and has a maximum depth 102b. Thereafter, the control system 106 may be used to maintain the depth 102b of drilling fluid 102 upstream of the apparatus 100 at a substantially constant level by controlling, either periodically or substantially continuously, the rotational speed of the drive motor 126 based on the sensor data obtained by the sensors 119a/b (and/or 120a/b) as previously described. In this way, the angular velocity of the rotating blade assembly 130 may be adjusted so that the depth 102b immediately upstream of the apparatus 100 remains substantially constant, and the flow rate of the drilling fluid 102 through the apparatus 100 can therefore be determined on substantially a real-time basis from the angular velocity of the blade assembly 130. In certain embodiments, the increased depth 102b of the drilling fluid 102 upstream of the apparatus 100 may tend to increase the level of overall flow control accuracy of the apparatus 100, which may thus provide an increased degree accuracy for the subsequently determined flow rate through the apparatus 100.

In at least some embodiments, as the rotating blade assembly 130 is rotated during operation, each of the blades 134 may pass through and across substantially the entire projected flow path that is defined between the fluid inlet 114 and the fluid outlet 116, that is, the blades 134 may sweep across substantially the full width and full height of the flow path through the apparatus 100. Due to this substantially complete sweeping motion of the blades 134, together with the previously noted close fit between the edges 134*e* of the blades 134 and the inside surfaces 118*s*/120*s* of the body 112, and/or the use of wipers (not shown) affixed to each blade 134, the build-up of a bed of stationary drill cuttings along the horizontally oriented bottom side 120*h* of the apparatus 100 may be substantially prevented. In this way, drill cuttings that normally tend to settle out of the fluid flow at the bottom the bottom of the conduit (e.g., the flow line 103 shown in FIG. 18) are swept through and out of the apparatus 100 by operation of the rotating blade assembly 130. Accordingly, the shortcomings of the prior art "paddle wheel" flow indicator may be substantially avoided when the apparatus 100 is operated as a flow meter, i.e., a flow measurement apparatus 100.

The above-described subject matter therefore discloses various systems, methods, and apparatuses that may be used to determine the flow rate of a fluid flowing through a conduit, such as, for example, a drilling fluid flow through a flow line of a drilling fluid circulation system. Furthermore, the present subject matter also discloses systems, methods, and apparatuses that may be used to automatically obtain samples of a fluid flowing through a conduit, e.g., a drilling fluid through a flow line.

The particular embodiments disclosed above are illustrative only, as the invention may be modified and practiced in different but equivalent manners apparent to those skilled in the art having the benefit of the teachings herein. For example, in at least some embodiments, the method steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. An apparatus, comprising:
   a body having a central axis;
   a fluid inlet coupled to said body, said fluid inlet being adapted to receive a flow of a fluid;
   a fluid outlet coupled to said body, said fluid outlet being adapted to receive at least a portion of said flow of said fluid from said fluid inlet, wherein said fluid inlet and said fluid outlet are substantially coaxially aligned so as to define a flow axis through said apparatus, said flow axis being laterally offset from and substantially perpendicular to said central axis of said body; and
   a rotating blade assembly disposed within said body and comprising a plurality of blades, wherein said rotating blade assembly is adapted to be continuously and controllably rotated about said central axis and to control a fluid level of said flow of said fluid entering said fluid inlet during said continuous and controlled rotation by variably adjusting an angular velocity of said rotating blade assembly.

2. The apparatus of claim 1, wherein said rotating blade assembly is adapted to be controllably rotated at an angular velocity that is proportional to a flow rate of a flow of a fluid flowing through said apparatus along said flow axis.

3. The apparatus of claim 1, wherein said rotating blade assembly is adapted to be continuously and controllably rotated so as to control a fluid level of a flow of a fluid entering said fluid inlet during said continuous and controlled rotation of said rotating blade assembly by at least one of increasing said fluid level and decreasing said fluid level.

4. The apparatus of claim 1, wherein said apparatus is adapted to receive a flow of a mixture of fluid and solids through said fluid inlet and said rotating blade assembly is adapted to sweep at least a portion of said fluid and at least a portion of said solids out of said apparatus through said fluid outlet.

5. The apparatus of claim 1, wherein at least some of said plurality of blades are substantially radially oriented with respect to said central axis.

6. The apparatus of claim 1, wherein each one of said plurality of blades is adapted to periodically at least partially restrict fluid communication between said fluid inlet and said fluid outlet.

7. The apparatus of claim 1, further comprising a drive motor coupled to said rotating blade assembly, said drive motor being adapted to continuously and controllably rotate said rotating blade assembly about said central axis.

8. The apparatus of claim 7, further comprising a control system that is operatively coupled to said drive motor, wherein said control system is adapted to variably adjust said angular velocity of said rotating blade assembly.

9. The apparatus of claim 8, further comprising at least one sensor that is adapted to obtain data on at least a flow level of a flow of a fluid flowing through said apparatus along said flow axis, wherein said at least one sensor is operatively coupled to said control system, and said control system is adapted to control said flow level.

10. The apparatus of claim 9, wherein said at least one sensor is coupled to said fluid inlet.

11. The apparatus of claim 1, further comprising a sample outlet disposed on said body, wherein said rotating blade assembly comprises at least one sample chamber that is adapted to receive a sample portion of a fluid flowing into said apparatus through said fluid inlet and discharge said received sample portion out of said apparatus through said sample outlet.

12. The apparatus of claim 11, wherein lateral sides of said at least one sample chamber are at least partially defined by an adjacent pair of said plurality of blades.

13. The apparatus of claim 11, wherein said at least one sample chamber comprises a chamber inlet that is adapted to be periodically in fluid communication with said fluid inlet so as to receive a sample portion of a fluid flowing into said apparatus therefrom and a chamber outlet that is adapted to be in fluid communication with said sample outlet so as to discharge said received sample portion therethrough.

14. The apparatus of claim 13, wherein said rotating blade assembly comprises a bottom support disk that is coupled to said at least one sample chamber and to each one of said plurality of blades.

15. An apparatus, comprising:
   a body having a central axis;
   a fluid inlet coupled to said body, said fluid inlet being adapted to receive a flow of a fluid;
   a fluid outlet coupled to said body, wherein said fluid inlet and said fluid outlet are substantially coaxially aligned so as to define a flow axis through said apparatus, said flow axis being laterally offset from and perpendicular to said central axis of said body;
   a sample outlet disposed on said body, wherein a central axis of said sample outlet is substantially coaxially aligned with said central axis of said body;
   a rotating blade assembly disposed within said body, wherein said rotating blade assembly comprises a plurality of blades and is adapted to receive a sample portion of said flow of said fluid entering said fluid inlet and to discharge said received sample portion out of said apparatus through said sample outlet.

16. The apparatus of claim 15, wherein said sample outlet is coupled to a bottom side of said body.

17. The apparatus of claim 15, wherein said rotating blade assembly is adapted to be continuously and controllably rotated about said central axis of said body so as to control a flow of a fluid flowing through said apparatus.

18. The apparatus of claim 17, wherein said rotating blade assembly is adapted to control a flow of a fluid flowing through said apparatus by periodically at least partially restricting fluid communication between said fluid inlet and said fluid outlet.

19. The apparatus of claim 15, further comprising:
a drive motor coupled to said rotating blade assembly, said drive motor being adapted to continuously and controllably rotate said rotating blade assembly;
at least one sensor that is operatively coupled to said apparatus, said at least one sensor being adapted to obtain data on at least a flow level of a flow of a fluid flowing through said apparatus; and
a control system that is operatively coupled to said drive motor and to said at least one sensor, said control system being adapted to receive said obtained data from said at least one sensor and control said drive motor so as to adjust an angular velocity of said rotating blade assembly based on said received data.

20. The apparatus of claim 15, wherein said rotating blade assembly comprises a sample chamber, said sample chamber comprising a chamber inlet that is adapted to receive a sample portion of a flow of a fluid flowing into said fluid inlet and a chamber outlet that is adapted to discharge said received sample portion to said sample outlet.

21. The apparatus of claim 20, wherein lateral sides of said sample chamber are at least partially defined by an adjacent pair of said plurality of blades.

22. The apparatus of claim 20, wherein said chamber inlet comprises an opening in one blade of said adjacent pair of said plurality of blades, said opening being positioned proximate an outside edge of said one blade.

23. The apparatus of claim 20, wherein an outer side of said sample chamber is at least partially defined by at least one chamber cover plate coupled to each one of said adjacent pair of said plurality of blades, a shape of said at least one chamber cover plate being configured so as to substantially conform to a shape of an inside surface of said body.

24. The apparatus of claim 15, wherein said rotating blade assembly further comprises a bottom support disk that is coupled to each one of said plurality of blades, said bottom support disk comprising an outlet opening that is adapted to discharge a sample portion of a flow of fluid that is received by said rotating blade assembly to said sample outlet.

25. The apparatus of claim 15, wherein said rotating blade assembly is adapted to be controllably rotated at an angular velocity that is proportional to a flow rate of a flow of a fluid flowing through said apparatus along said flow axis.

26. The apparatus of claim 15, wherein said rotating blade assembly is adapted to be controllably rotated so as to control a fluid level of a flow of a fluid entering said fluid inlet by at least one of increasing said fluid level and decreasing said fluid level.

27. The apparatus of claim 15, wherein said rotating blade assembly comprises a sample chamber that is adapted to receive a sample portion of a flow of fluid entering said fluid inlet, said rotating blade assembly being adapted to enable a gravity-assisted flow of said sample portion from said sample chamber to said sample outlet as said sample chamber is rotated from a position horizontally adjacent to said sample outlet to a position vertically above said sample outlet.

28. A method of operating a flow apparatus, the method comprising:
introducing a flow of a flow mixture to a fluid inlet of said flow apparatus, wherein said fluid inlet is coupled to a body of said flow apparatus and comprises a flow axis that is laterally offset from and substantially perpendicular to a central axis of said body; and
controlling a fluid level of said flow of said flow mixture introduced to said fluid inlet, wherein controlling said fluid level comprises at least one of increasing said fluid level and decreasing said fluid level by continuously and controllably rotating a rotating blade assembly comprising a plurality of blades and disposed within said body about said central axis while flowing said flow of said flow mixture through said flow apparatus from said fluid inlet to a fluid outlet of said flow apparatus, and wherein continuously and controllably rotating said rotating blade assembly comprises variably adjusting an angular velocity of said rotating blade assembly.

29. The method of claim 28, wherein continuously and controllably rotating said rotating blade assembly comprises coupling a drive motor to said rotating blade assembly and continuously and controllably rotating said rotating blade assembly with said drive motor while flowing said flow of said flow mixture through said flow apparatus from said fluid inlet to said fluid outlet.

30. The method of claim 29, wherein controlling said fluid level of said flow of said flow mixture through said flow apparatus comprises providing at least one sensor and obtaining data on said flow of said flow mixture into said flow apparatus with said at least one sensor.

31. The method of claim 30, wherein obtaining said data on said flow of said flow mixture into said flow apparatus comprises obtaining at least one of a pressure and a fluid level of said flow of said flow mixture.

32. The method of claim 30, wherein controlling said fluid level of said flow of said flow mixture through said flow apparatus further comprises operatively coupling a control system to said drive motor and said at least one sensor and adjusting said angular velocity of said rotating blade assembly by controlling a rotational speed of said drive motor based on said obtained data.

33. The method of claim 28, wherein continuously and controllably rotating said rotating blade assembly comprises measuring a flow rate of said flow of said flow mixture through said flow apparatus.

34. The method of claim 28, wherein controlling said flow of said flow mixture through said flow apparatus comprises periodically at least partially restricting fluid communication between said fluid inlet and said fluid outlet of said flow apparatus with at least one of said plurality of blades, said fluid outlet being substantially coaxially aligned with said fluid inlet.

35. The method of claim 28, wherein said flow mixture comprises a mixture of fluid and solids, the method further comprising continuously sweeping at least a portion of said fluid and at least a portion of said solids out of said flow apparatus through said fluid outlet of said flow apparatus with at least one of said plurality of blades, said fluid outlet being substantially coaxially aligned with said fluid inlet.

36. The method of claim 28, further comprising receiving a sample portion of said flow of said flow mixture with said rotating blade assembly while flowing said flow of said flow mixture through said flow apparatus and discharging said sample portion from said rotating blade assembly through a sample outlet disposed on said body.

37. The method of claim 36, wherein receiving said sample portion of said flow of said flow mixture with said rotating blade assembly comprises receiving said sample portion through a chamber inlet of a sample chamber comprising said rotating blade assembly and wherein discharging said sample portion from said rotating blade assembly through said sample outlet comprises discharging said sample portion through a chamber outlet of said sample chamber, said sample chamber being at least partially defined by an adjacent pair of said plurality of blades.

\* \* \* \* \*